(12) United States Patent
Wu et al.

(10) Patent No.: US 12,164,011 B2
(45) Date of Patent: Dec. 10, 2024

(54) SYSTEM AND METHOD FOR FREE-BREATHING QUANTITATIVE MULTIPARAMETRIC MRI

(71) Applicant: The Regents of the University of California, Oakland, CA (US)

(72) Inventors: Holden H. Wu, Los Angeles, CA (US); Le Zhang, Los Angeles, CA (US); Tess Armstrong, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 34 days.

(21) Appl. No.: 17/602,926

(22) PCT Filed: Apr. 15, 2020

(86) PCT No.: PCT/US2020/028345
§ 371 (c)(1),
(2) Date: Oct. 11, 2021

(87) PCT Pub. No.: WO2020/214725
PCT Pub. Date: Oct. 22, 2020

(65) Prior Publication Data
US 2022/0179023 A1 Jun. 9, 2022

Related U.S. Application Data

(60) Provisional application No. 62/833,894, filed on Apr. 15, 2019.

(51) Int. Cl.
*G01R 33/48* (2006.01)
*A61B 5/00* (2006.01)
(Continued)

(52) U.S. Cl.
CPC ........ *G01R 33/4826* (2013.01); *A61B 5/0036* (2018.08); *A61B 5/015* (2013.01);
(Continued)

(58) Field of Classification Search
CPC ............ G01R 33/4826; G01R 33/4804; G01R 33/4828; G01R 33/50; G01R 33/5616;
(Continued)

(56) References Cited

U.S. PATENT DOCUMENTS

| 8,989,465 | B2 | 3/2015 | Trzasko et al. |
| 9,971,003 | B2 * | 5/2018 | Köhler ............... G01R 33/4804 |

(Continued)

FOREIGN PATENT DOCUMENTS

| EP | 2518523 A1 * | 10/2012 | ......... G01R 33/4804 |

OTHER PUBLICATIONS

Svedin, Bryant T., Allison Payne, and Dennis L. Parker. "Simultaneous proton resonance frequency shift thermometry and T1 measurements using a single reference variable flip angle T1 method." Magnetic resonance in medicine 81.5 (2018): 3138-3152. (Year: 2018).*

(Continued)

*Primary Examiner* — Rishi R Patel
(74) *Attorney, Agent, or Firm* — Quarles & Brady LLP

(57) ABSTRACT

A method for proton resonance frequency shift (PRF) and $T_1$-based temperature mapping using a magnetic resonance imaging (MRI) system includes acquiring, using the MRI system, a set of magnetic resonance (MR) data from a region of interest of a subject by performing a variable-flip-angle multi-echo gradient-echo 3D stack-of-radial pulse sequence. The pulse sequence is configured to acquire radial k-space data in a plurality of segments, each segment acquired with each of a plurality of flip angles. The method further includes generating at least one $T_1$ map based on the set of MR data, generating at least one PRF temperature map based on the set of MR data, generating at least one $T_1$-based temperature map based on the set of MR data and displaying the PRF temperature map and the $T_1$-based temperature (Continued)

map. In another embodiment, the MR data may be used to generate a plurality of quantitative parameter maps for each of the plurality of MR parameters such as $T_1$, proton-density fat fraction (PDFF), and $R_2^*$.

12 Claims, 22 Drawing Sheets

(51) Int. Cl.
*A61B 5/01* (2006.01)
*A61B 5/055* (2006.01)
*G01R 33/50* (2006.01)
*G01R 33/54* (2006.01)
*G01R 33/561* (2006.01)

(52) U.S. Cl.
CPC .......... *A61B 5/055* (2013.01); *G01R 33/4804* (2013.01); *G01R 33/4828* (2013.01); *G01R 33/50* (2013.01); *G01R 33/5616* (2013.01); *A61B 2576/00* (2013.01); *G01R 33/543* (2013.01)

(58) Field of Classification Search
CPC .......... G01R 33/543; G01R 33/5676; A61B 5/0036; A61B 5/015; A61B 5/055; A61B 2576/00; A61B 5/318; A61B 5/0037; A61B 5/0816; A61B 5/113; A61B 5/1135; A61B 5/7285
See application file for complete search history.

(56) References Cited

U.S. PATENT DOCUMENTS

| | | | | |
|---|---|---|---|---|
| 2014/0142417 | A1* | 5/2014 | Reeder ................ | A61B 5/055 600/420 |
| 2017/0035301 | A1* | 2/2017 | Lechner-Greite .... | A61B 5/7285 |
| 2017/0322274 | A1* | 11/2017 | Bolster, Jr. ......... | G01R 33/5615 |
| 2018/0132787 | A1 | 5/2018 | Leporq et al. | |

OTHER PUBLICATIONS

Zhang, Le, et al. "A variable flip angle golden-angle-ordered 3D stack-of-radial MRI technique for simultaneous proton resonant frequency shift and T1-based thermometry." Magnetic resonance in medicine 82.6 (Jun. 2019): 2062-2076. (Year: 2019).*

Zhang, Le, et al. "Hybrid Proton Resonance Frequency Shift and Variable Flip Angle T1 Temperature Mapping using a Golden-Angle 3D Stack-of-Radial Technique." (Year: 2018).*

Zhang et al., Hybrid Proton Resonance Frequency Shift and Variable Flip Angle T1 Temperature Mapping Using a Golden-Angle 3D Stack-of-Radial Technique, Proceedings of the International Society for Magnetic Resonance in Medicine, 26th Annual Meeting and Exhibition, 2018, 26:1494, 6 pages.

European Patent Office, Extended Search Report, Application No. 20792234.5, Sep. 14, 2023, 14 pages.

Svedin et al., Multiecho Pseudo-Golden Angle Stack of Stars Thermometry with High Spatial and Temporal Resolution Using k-Space Weighted Image Contrast, Magnetic Resonance in Medicine, 2018, 79(3):1407-1419.

PCT International Search Report and Written Opinion, PCT/US2020/028345, Jul. 2, 2020, 9 pages.

Armstrong T., et al., Free-Breathing Liver Fat Quantification Using a Multiecho 3D Stack-of-Radial Technique, Magnetic Resonance in Medicine, 2018; 79(1): 370-82.

Hey S., et al., Simultaneous T1 measurements and proton respnance frequency shift based thermometry using variable flip angles, Magnetic Resonance in Medicine, 2012: 67(2): 457-463.

Todd N., et al. Hybrid proton resonance frequency/T1 technique for simultaneous temperature monitoring in adipose and acqueous tissues, Magnetic Resonance in Medicine, 2013; 60(1): 62-70.

Todd, N. In vivo evaluation of multi-echo hybrid PRF/T1 approach for temperature monitoring during breast MR-guided focused ultrasound surgery treatments, Magnetic Resonance in Medicine, 2014; 72(3): 793-799.

* cited by examiner

SYSTEM AND METHOD FOR FREE-BREATHING QUANTITATIVE MULTIPARAMETRIC MRI

CROSS-REFERENCE TO RELATED APPLICATION

This application represents the national stage entry of International Application No. PCT/US2020/028345, filed Apr. 15, 2020 which claims the benefit of and priority to U.S. Ser. No. 62/833,894 filed Apr. 15, 2019 and entitled "Method and Apparatus for Quantitative Multiparametric MRI", which is incorporated herein by reference in its entirety.

BACKGROUND

Magnetic resonance imaging (MRI) provides crucial information to plan, guide, monitor, and assess minimally invasive thermal therapy modalities, including high-intensity focused ultrasound (HIFU), radiofrequency (RF) ablation, microwave ablation, and laser interstitial thermal therapy (LITT). These thermal therapy modalities may be used, for example, to treat an array of cancers by inducing tissue necrosis with sustained treatment. Among these modalities, MRI-guided HIFU is especially attractive since both MRI and HIFU are non-invasive and can access tissues deep in the body for treating various conditions such as breast and prostatic cancers. The anatomical information from MRI can facilitate treatment planning. Most importantly, MR thermometry can measure temperature distribution and estimate thermal dosage during procedures to help determine the treatment endpoint while providing safety information to avoid unwanted thermal damage outside of the treatment zone.

The most widely used strategy for MR temperature mapping is based on the proton resonance frequency shift (PRF), which decreases linearly with temperature with a coefficient of −0.01 ppm/° C., stays consistently over a wide temperature range relevant to thermal therapy and is independent of tissue types. By measuring the change in the accumulated phase in a gradient echo sequence during heating with respect to a baseline map without heating, PRF methods can map temperature. However, PRF temperature mapping is susceptible to phase errors and image artifacts caused by motion, such as respiratory, cardiac and peristaltic motion or bulk patient movement, which may cause a mismatch between the heated and baseline maps and can lead to temperature errors. In moving organs, such as the liver, respiratory and cardiac motion can cause mis-registration in phase images, and lead to erroneous temperature results. Improved PRF techniques have been proposed to either use a library of baseline images at different motion states to account for periodic motion or eliminate the need of baseline images altogether. In addition, the effects of motion have been addressed by using navigator echoes, respiratory gating, and referenceless phase correction.

A second drawback of PRF thermometry is that the proton resonance frequency of fat spins only displays a minute temperature dependence due to the lack of hydrogen bonds, and cannot be used to measure temperature change in adipose tissues. Lipid suppression and chemical-shift-based water/fat separation methods have been developed to reduce PRF temperature errors in voxels that contain both water and fat. Nonetheless, it is often crucial to have thermal information to avoid burns in predominantly-fat voxels where heat dissipates more slowly, such as in the breasts and abdomen. Fortunately, various other MR parameters are sensitive to temperature changes. One promising approach is to simultaneously quantify $T_1$ relaxation time along with PRF to provide dual temperature measurements in both aqueous and adipose tissues.

A variable flip angle (VFA) scheme provides fast $T_1$ mapping and can be implemented with Cartesian MRI sequences for simultaneous PRF/$T_1$ thermometry. Since the signal model for VFA $T_1$ mapping requires accurate knowledge of the flip angles, additional measurement of the $B_1+$ field is needed. Due to the lengthened acquisition time for multiple flip angles, VFA PRF/$T_1$ methods are typically either confined to a single 2D slice or a thin 3D slab with limited through-plane coverage to achieve the desired temporal resolution. This shortcoming renders it difficult to achieve a field-of-view (FOV) that encompasses larger lesions and surrounding tissues such as in the liver, or to monitor and avoid unwanted heating in both the near- and far-field of the HIFU transducer. Therefore, VFA PRF/$T_1$ methods could be improved by incorporating more efficient sampling strategies and/or undersampling in combination with advanced reconstruction, including segmented 3D echo-planar imaging (EPI), simultaneous multiple slice acquisition, direct estimation from undersampled k-space data, and temporally constrained reconstruction.

Non-Cartesian sampling schemes, such as the golden-angle (GA) ordered 3D stack-of-radial trajectory, have higher tolerance to undersampling and thus can achieve high temporal resolution while providing large 3D spatial coverage. The 3D stack-of-radial trajectory also improves robustness to motion since it disperses its effects along all radial directions instead of one axis in Cartesian sampling. The repeatedly sampled data at the center of k-space can also be used as a self-navigator to detect and compensate for motion. The azimuthal angle for radial readouts can be continuously incremented by the GA of 111.246° to sample k-space in an efficient fashion, and offers flexibility in choosing sets of radial angles during reconstruction to adjust the temporal resolution. A hybrid GA-ordered radial acquisition scheme with EPI encoding in the through-plane dimension was developed for volumetric PRF thermometry coverage. Using a GA-ordered 3D stack-of-radial trajectory with multi-echo gradient-echo readouts, another scheme reconstructed separate fat and water images to apply PRF specifically in aqueous tissues in breasts during HIFU ablation. Further improvements in temporal resolution were achieved by employing partial Fourier along the Cartesian-encoded slice direction and using a k-space-weighted image contrast (KWIC) filter.

MRI may also be used as a non-invasive, non-ionizing tool for diagnosing disease of specific anatomy, for example, the liver. Proton-density fat fraction (PDFF) and $R_2^*$ relaxation time measurements are used for the clinical diagnosis of, for example, hepatic steatosis and iron accumulation, respectively. For the detection of liver fibrosis, several MRI contrast mechanisms have been developed for potential clinical use. Diffusion weighted imaging (DWI) can characterize the restriction of water diffusion due to fibrosis. However, DWI faces challenges such as low image quality and cardiac and breathing motion artifacts. Moreover, the measured apparent diffusion coefficient has not been shown to be a reliable indicator of the fibrosis stage. MR elastography (MRE) measures liver stiffness by detecting the propagation of shear waves through the liver using motion-sensitive MRI sequences and can discriminate between various fibrosis stages. The accuracy of MRE for detecting and staging liver fibrosis has been validated by biopsy.

While MRE is a valuable clinical tool, MRE can encounter measurement difficulties in patients with increased hepatic iron content, which is present in up to one-third of patients with diffusive liver diseases such as non-alcoholic fatty liver disease (NAFLD). Iron in itself can contribute to liver fibrosis, and may cause a decrease in the accuracy of stiffness measurements due to the effects of $T_2^*$ shortening on gradient-echo based MRE protocols. In addition, the specialized hardware required for MRE may not be available at all institutions or practical for young children and infants.

Another emerging quantitative MRI biomarker of fibrosis is $T_1$ relaxation time of the liver. To investigate liver function, $T_1$-weighted images may be acquired after the injection of gadoxetic acid or gadoxetate disodium to characterize the association between fibrosis and the increased concentration in the liver of the $T_1$-shortening contrast agents. However, the administration of contrast agents requires intravenous injection and takes additional time. Moreover, it may not be feasible in patients with renal deficiency and diseases. Recently, it has been proposed that the direct measurement of liver $T_1$ relaxation times may be more robust than the calculation of the relative enhancement or enhancement index of the $T_1$-weighted signal intensity, which may vary considerably with different imaging or technical factors. In addition, because the native $T_1$ of the liver can be prolonged by liver fibrosis, several studies have investigated native $T_1$ as a quantitative biomarker without contrast agents, using $T_1$ mapping techniques such as Modified Look-Locker Inversion Recovery (MOLLI) and TurboFLASH.

In addition to fibrosis, fat and iron content in the liver also impact the $T_1$ measurements. Moreover, it has been reported that combined fatty liver and iron overload can lead to worse outcomes than fatty liver alone. As a result, multiparametric mapping and joint consideration of $T_1$, PDFF, and $R_2^*$ has the potential to provide simultaneous information for characterizing hepatic steatosis, fibrosis, and iron overload, which could in turn be important for diagnosing a variety of liver diseases. Simultaneous mapping of liver $T_1$, PDFF, and $R_2^*$ has been achieved with a Cartesian trajectory with multi-echo gradient-echo readouts. Because the liver moves with respiration and Cartesian sampling is sensitive to motion artifacts, images are acquired during breath-holding. However, breath-holding is challenging. Sick, young, and elderly patients often cannot breath-hold or have imperfect breath-holding, which can result in poor image quality and quantification errors. While a high acceleration factor can be used to facilitate Cartesian acquisition during a short breath-hold duration, this may lead to artifacts and quantification errors.

SUMMARY OF THE DISCLOSURE

In accordance with an embodiment, a method for proton resonance frequency shift (PRF) and $T_1$-based temperature mapping using a magnetic resonance imaging (MRI) system includes acquiring, using the MRI system, a set of magnetic resonance (MR) data from a region of interest of a subject by performing a variable-flip-angle multi-echo gradient-echo 3D stack-of-radial pulse sequence. The pulse sequence is configured to acquire radial k-space data in a plurality of segments, each segment acquired with each of a plurality of flip angles. The method further includes generating at least one $T_1$ map based on the set of MR data, generating at least one PRF temperature map based on the set of MR data, generating at least one $T_1$-based temperature map based on the set of MR data, and displaying the PRF temperature map and the $T_1$-based temperature map.

In accordance with another embodiment, a method for quantifying a plurality of magnet resonance (MR) parameters using a magnetic resonance imaging (MRI) system includes acquiring, using the MRI system, a set of magnetic resonance (MR) data from a region of interest of a subject by performing a variable-flip-angle multi-echo gradient-echo 3D stack-of-radial pulse sequence. The pulse sequence is configured to acquire radial k-space data in a plurality of segments, each segment acquired with each of a plurality of flip angles. The method further includes generating a plurality of quantitative parameter maps for each of the plurality of MR parameters based on the set of MR data, and displaying plurality of quantitative parameter maps for each of the plurality of MR parameters. The set of MR data may be used to generate fat maps, water maps, $T_1$ maps, proton-density fat fraction maps, and $R_2^*$ maps.

In accordance with another embodiment, a magnetic resonance imaging system includes a magnet system configured to generate a polarizing magnetic field about at least a portion of a subject, a magnetic gradient system including a plurality of magnetic gradient coils configured to apply at least one magnetic gradient field to the polarizing magnetic field, a radio frequency (RF) system configured to apply an RF field to the subject and to receive magnetic resonance signals from the subject using a coil array, and a computer system. The computer system is programmed to acquire a set of magnetic resonance (MR) data from a region of interest of a subject by performing a variable-flip-angle multi-echo gradient-echo 3D stack-of-radial pulse sequence. The pulse sequence is configured to acquire radial k-space data in a plurality of segments, each segment acquired with each of a plurality of flip angles. The computer system is further programmed to generate at least one $T_1$ map based on the set of MR data, generate at least one PRF temperature map based on the set of MR data, generate at least one $T_1$-based temperature map based on the set of MR data, and display the PRF temperature map and the $T_1$-based temperature map.

In accordance with another embodiment, a magnetic resonance imaging system includes a magnet system configured to generate a polarizing magnetic field about at least a portion of a subject, a magnetic gradient system including a plurality of magnetic gradient coils configured to apply at least one magnetic gradient field to the polarizing magnetic field, a radio frequency (RF) system configured to apply an RF field to the subject and to receive magnetic resonance signals from the subject using a coil array, and a computer system. The computer system is programmed to acquire a set of magnetic resonance (MR) data from a region of interest of a subject by performing a variable-flip-angle multi-echo gradient-echo 3D stack-of-radial pulse sequence. The pulse sequence is configured to acquire radial k-space data in a plurality of segments, each segment acquired with each of a plurality of flip angles. The computer system is further programmed to generate a plurality of quantitative parameter maps for each of the plurality of MR parameters based on the set of MR data, and display plurality of quantitative parameter maps for each of the plurality of MR parameters. The set of MR data may be used to generate fat maps, water maps, $T_1$ maps, proton-density fat fraction maps, and $R_2^*$ maps.

BRIEF DESCRIPTION OF THE DRAWINGS

The present invention will hereafter be described with reference to the accompanying drawings, wherein like reference numerals denote like elements.

DETAILED DESCRIPTION

Figure 1:
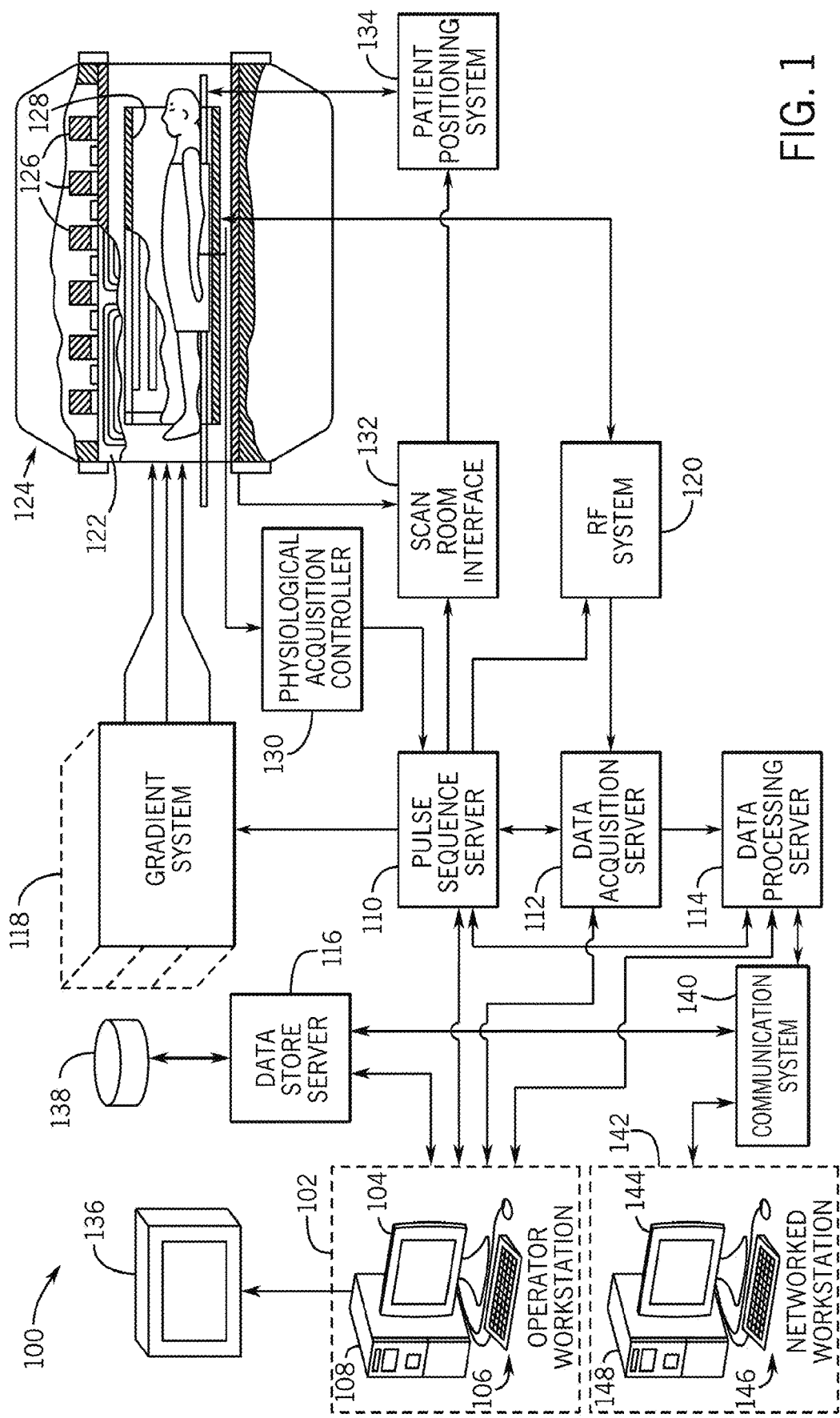
FIG. 1 is a schematic diagram of an example MRI system in accordance with an embodiment.

FIG. 1 shows an example of an MRI system 100 that may be used to perform the methods described herein. MRI system 100 includes an operator workstation 102, which may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$, that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \quad (1)$$

and the phase of the received magnetic resonance signal may also be determined according to the following relationship:

$$\varphi = \tan^{-1}\left(\frac{Q}{I}\right) \quad (2)$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

The present disclosure describes systems and methods for free-breathing quantitative multiparametric MRI. In particular, the present disclosure describes a variable flip angle (VFA) golden-angle-ordered (GA) three-dimensional (3D) stack-of-radial MRI technique that may be used to simultaneously generate quantitative parameter maps for multiple MR parameters. The disclosed VFA 3D stack-of-radial technique may be used to improve MRI-guided thermal procedures and to generate maps of multiple MR parameters from data acquired during free-breathing. In one embodiment, the VFA 3D stack-of-radial technique may be used for simultaneous proton resonant frequency shift (PRF) and $T_1$-based thermometry in aqueous and adipose tissues. The VFA 3D stack-of-radial technique acquires multi-echo radial k-space data in segments with alternating flip angles and uses the acquired data to dynamically measure 3D temperature maps based on PRF and $T_1$. Combined PRF/$T_1$ thermometry may be used in moving organs to provide volumetric coverage and high spatio-temporal resolution. In another embodiment, the VFA 3D stack-of-radial technique may be used to perform simultaneous quantification of proton-density fat fraction (PDFF), $R_2^*$, and $T_1$ during a free-breathing acquisition, e.g., in the liver. In this embodiment, the VFA 3D stack-of-radial technique may be used to map $T_1$, PDFF, and $R_2^*$ simultaneously with close to full anatomy coverage in a short scan time during free-breathing. For example, the VFA 3D stack-of-radial technique can quantify liver $T_1$, $R_2^*$ and PDFF in a single free-breathing scan under five minutes.

Figure 2:
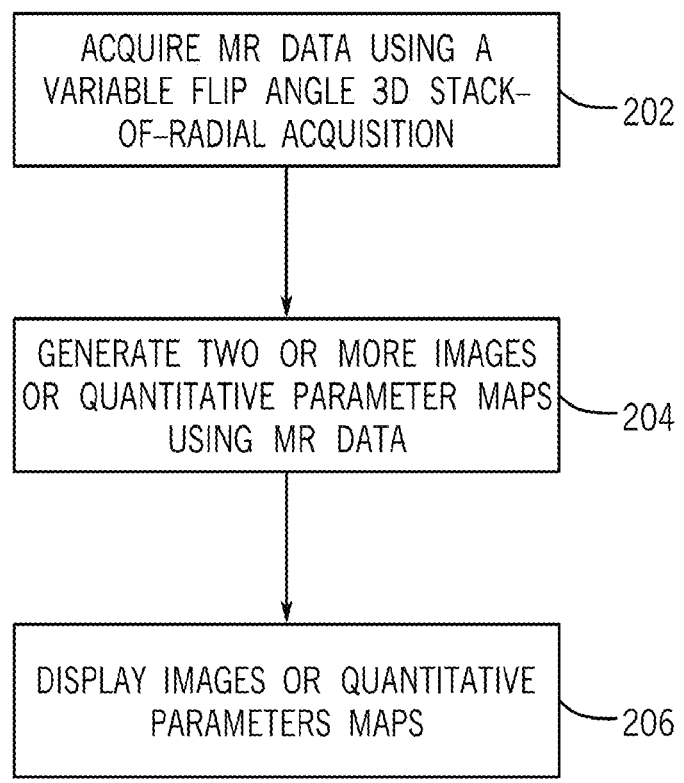
FIG. 2 illustrates a method for free-breathing quantitative multiparametric MRI in accordance with an embodiment.

FIG. 2 illustrates a method for free-breathing quantitative multiparametric MRI in accordance with an embodiment. At block 202, MR data is acquired from a region of interest in a subject using, for example, an MRI system (e.g., MRI system 100 shown in FIG. 1). The MR data is acquired using a variable flip angle (VFA) golden-angle-ordered (GA) three-dimensional (3D) stack-of-radial technique. In one embodiment, the VFA 3D stack-of-radial technique is used with a multi-echo gradient echo pulse sequence to acquire the MR data. At block 204, the MR data is used to generate two or more images or quantitative parameter maps for multiple MR parameters. As mentioned above, the MR data may be used for simultaneous PRF and $T_1$ temperature mapping or simultaneous proton-density fat fraction (PDFF), $R_2^*$, and $T_1$ mapping. The images or quantitative parameter maps may be reconstructed using, for example, the methods described herein below. At block 206, images or quantitative parameter maps may be provided to and shown on a display (e.g., display 104, 136 or 144 shown in FIG. 1). The MR data and generated images or quantitative parameter maps may be stored in memory or data storage of, for example, an MRI system (e.g., the MRI system 100 of FIG. 1) or other computer system.

Figure 3A:
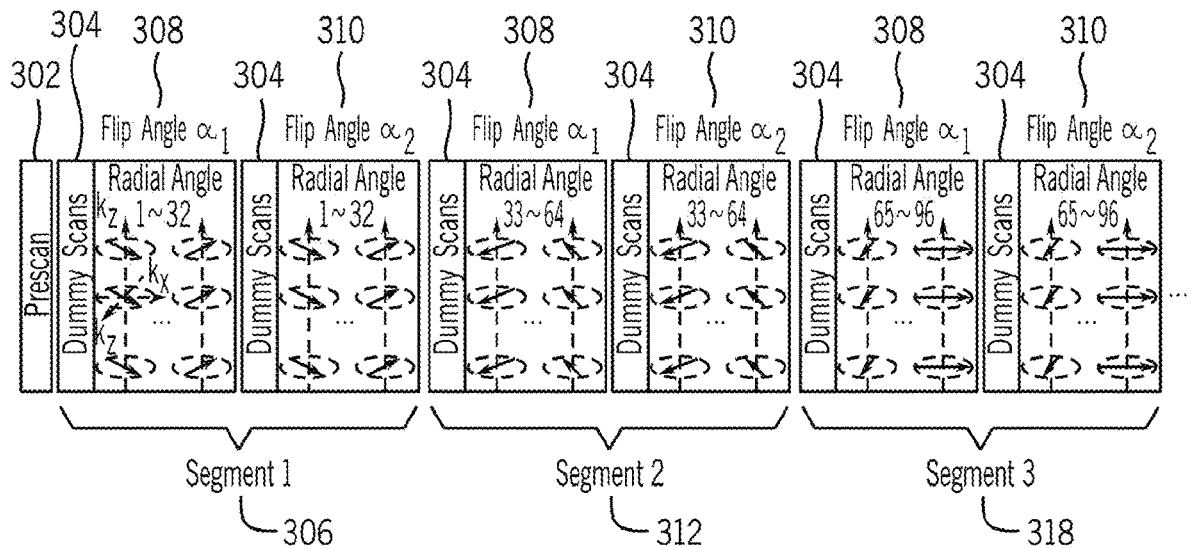
FIG. 3A illustrates a variable flip angle (VFA) golden-angle (GA) ordered 3D stack-of-radial MRI technique in accordance with an embodiment.
Figure 3B:
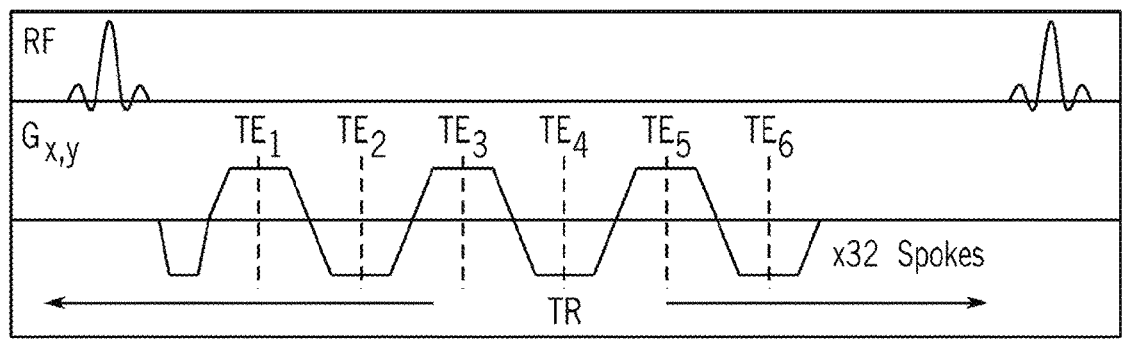
FIG. 3B illustrates an example multi-echo gradient echo acquisition for each radial angle in the VFA golden-angle (GA) ordered 3D stack-of-radial MRI technique of FIG. 3A in accordance with an embodiment.

FIG. 3A illustrates a variable flip angle (VFA) golden-angle (GA) ordered 3D stack-of-radial MRI technique in accordance with an embodiment and FIG. 3B illustrates an example multi-echo gradient echo acquisition for each radial angle in the VFA golden-angle (GA) ordered 3D stack-of-radial MRI technique of FIG. 3A in accordance with an embodiment. The VFA multi-echo gradient echo 3D stack-of-radial sequence ("radial VFA") 300 uses radial sampling in the $k_x$-$k_y$ plane and Cartesian encoding along $k_z$. The total prescribed number of radial angles are segmented into smaller sets of readouts, with the acquisition of each segment repeated with different flip angles. In other words, the sequence includes the segmented acquisition of radial spokes with variable flip angles $\alpha_i$. For example, as shown in FIG. 3A, a first segment 306 includes radial angles 1-32, a second segment 312 includes radial angles 33-64 and a third segment 318 includes radial angles 65-96. The first segment 306 is acquired at a first flip angle $\alpha_1$ 308 and a second flip angle $\alpha_2$ 310. The second segment 312 is acquired at a first flip angle $\alpha_1$ 308 and a second flip angle $\alpha_2$ 310. The third segment 318 is acquired at a first flip angle $\alpha_1$ 308 and a second flip angle $\alpha_2$ 310. The use of two flip angles may improve temporal resolution. While FIG. 3A illustrates the use of two flip angles $\alpha_1$ 308 and $\alpha_2$ 310, it should be understood that in other embodiments other numbers of different flip angles may be used. Each radial readout (i.e., spoke) is acquired with a bipolar multi-echo readout gradient 324 as shown in FIG. 3B. The example bipolar multi-echo gradient echo readout 324 includes six echoes, although other numbers of echoes may be used. Returning to FIG. 3A, after acquiring all slice-encoding steps for a given radial angle in a segment 306, 312, 318, the radial angle is incremented by the GA ($\theta_G$=111.246°) for the next set of readouts. The GA increment for radial angle ordering is continued across consecutive segments so that the readouts may be flexibly combined for dynamic image reconstruction. Other types of radial angle ordering and increment strategies may also be used. Dummy scans 304 (spokes with radial angle of 0°) are performed between flip angles (e.g., $\alpha_1$ 308 and $\alpha_2$ 310) to establish steady state for the spoiled gradient-echo signal at a particular flip angle. The dummy scans 304 are not used for image reconstruction. The bipolar multi-echo radial sampling strategy described with respect to FIGS. 3A and 3B may be sensitive to gradient delays and eddy currents, which cause an apparent shift of k-space readouts. In an embodiment, a prescan 302 including additional readouts with radial angles of 0°, 90°, 180° and 270° is acquired at the beginning of the scan to calibrate such shifts and correct the data to compensate for these effects.

Figure 4A:
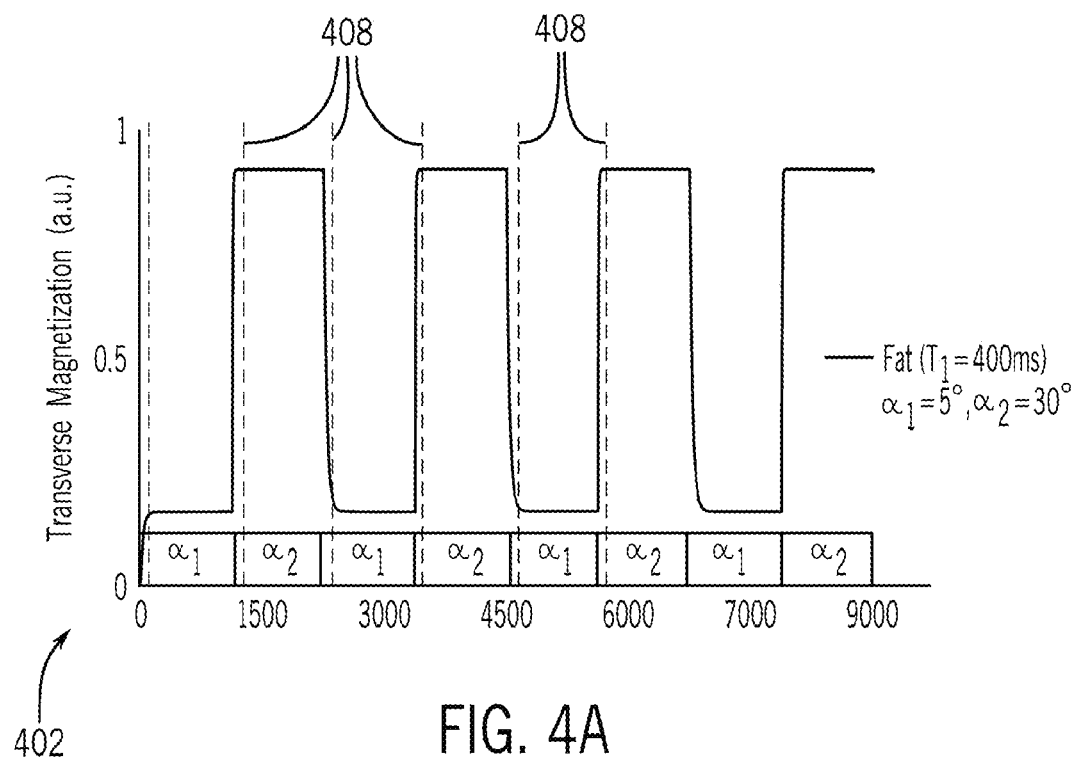
FIG. 4A shows example Bloch simulation of the transient state for the VFA 3D stack-of-radial radial technique in fat in accordance with an embodiment.
Figure 4B:
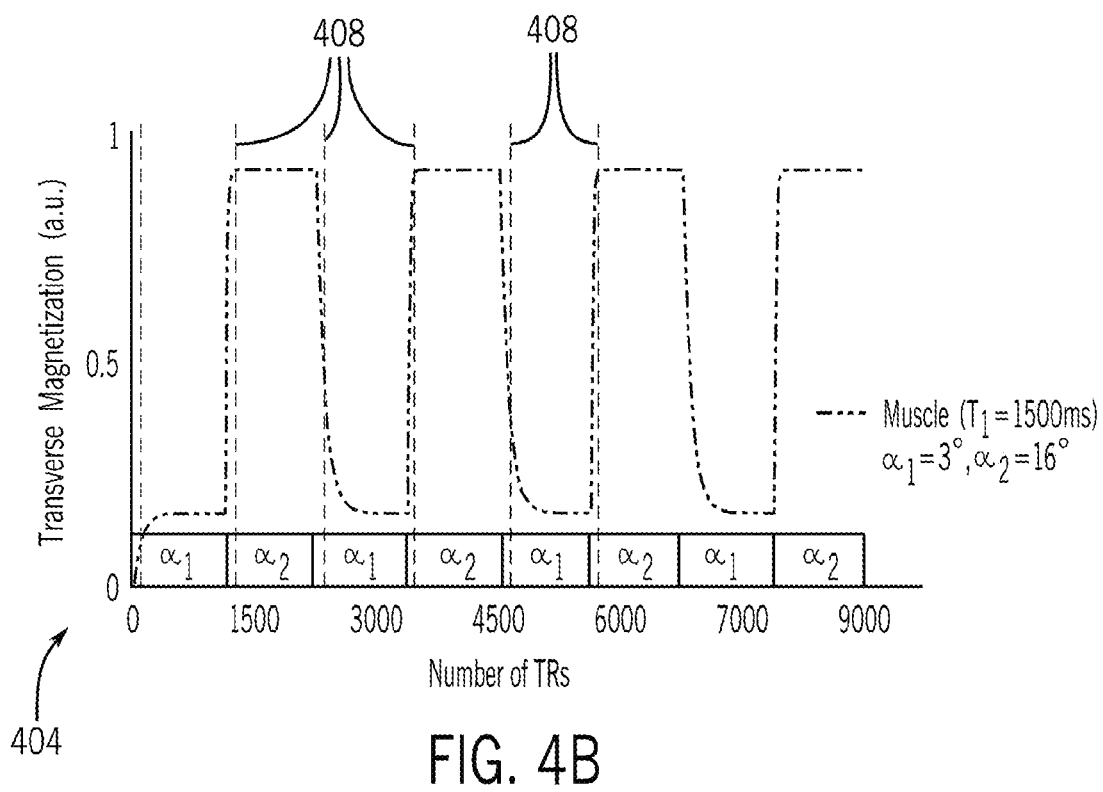
FIG. 4B shows example Bloch simulations of the transient state for the VFA 3D stack-of-radial technique in muscle (b) in accordance with an embodiment.

In an embodiment, the number of dummy scans needed to establish steady state for each segment may be determined using Bloch simulations performed using a single-echo spoiled gradient-echo sequence to study evolution of transverse magnetization of both fat and water spins as flip angles are being switched between segments. FIG. 4A shows example Bloch simulation of the transient state for the VFA 3D stack-of-radial radial technique in fat in accordance with an embodiment and FIG. 4B shows example Bloch simulations of the transient state for the VFA 3D stack-of-radial technique in muscle, in accordance with an embodiment. In the example of FIGS. 4A and 4B, the parameters used were: 3D slab RF excitation; TE=1.5 ms; TR=10 ms; 32 slices; 1024 readouts (i.e., TRs) per flip angle per segment; 4 segments. For a fat simulation 402 with $T_1$=400 ms, 5° and 30° were chosen as the flip angles. For a muscle simulation 404 with $T_1$=1500 ms, 3° and 16° were chosen. For simulations of fat 402, the parameters were $T_1/T_2$=400/70 ms and frequency offset=420 Hz at 3 T, and for simulation of muscle 404, $T_1/T_2$=1500/100 ms and frequency offset=0 Hz. For long $T_1$ species such as muscle, more TRs are needed for the spins to fully enter steady state after each switch of flip angles than for species with short $T_1$, such as fat, especially from $\alpha_2$ to $\alpha_1$, where $\alpha_2 > \alpha_1$. In the examples shown in FIGS. 4A and 4B, the steady state is established approximately 128 repetition times (TR) after switching the flip angle (α). The dashed lines 408 represent 128 TRs after each flip angle switch, by which time the signal from fat and water spins may be deemed to have sufficiently entered steady state, and may be chosen as the number of dummy scans. In an embodiment using a 3D slab excitation, when 32 slices are used only four sets of dummy scans are needed at the beginning of each segment before actual GA-ordered radial spokes are sampled.

Figure 5:
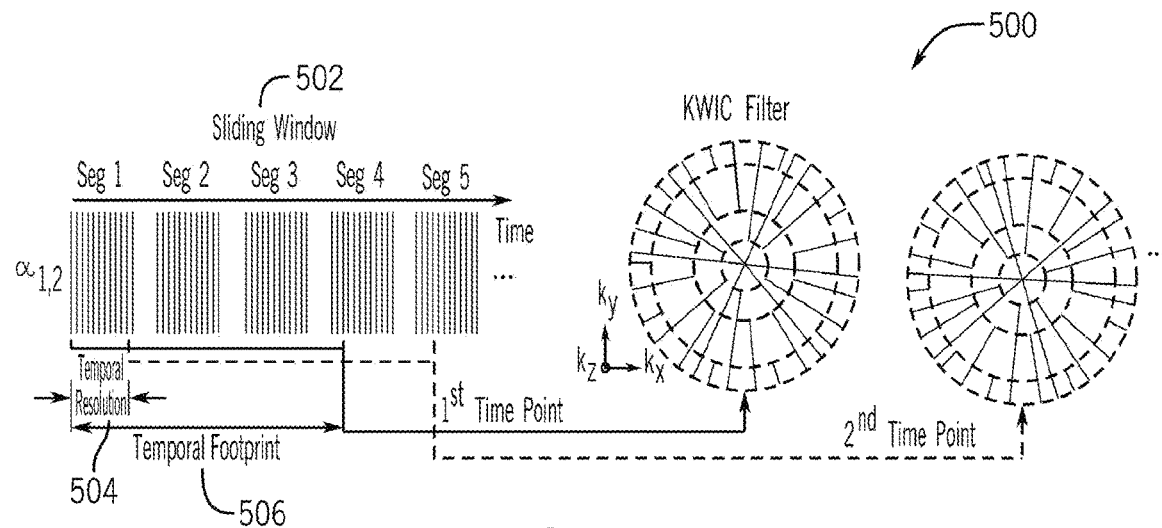
FIG. 5 illustrates a backward-looking sliding-window k-space weighted image contrast (KWIC) filter for use in reconstruction in accordance with an embodiment.

As mentioned, the VFA 3D stack-of-radial technique may be used for simultaneous proton resonant frequency shift (PRF) and $T_1$-based thermometry in aqueous and adipose tissues. In this embodiment, the reconstruction pipeline may employ a backward-looking sliding-window k-space weighted image contrast (KWIC) filter as illustrated in FIG. 5. The KWIC filter 500 is used for each flip angle for dynamic image reconstruction. In one example, a total of seven annular regions were used for the KWIC filter 500 for each image frame, with the number of radial spokes in each annulus following the Fibonacci numbers. The resulting k-space data may then be reconstructed using 3D gridding and density compensation with a Voronoi filter. The pre-scan noise adjustment data is used to calculate a noise covariance matrix for coil elements, which may then be used during coil combination to improve signal-to-noise ratio (SNR) of the combined images. The KWIC filter 500 may then be advanced in a sliding-window 502 fashion to produce dynamic images (magnitude and phase) with a step size that is equal to the number of radial angles in the innermost annulus of the KWIC filter. In an embodiment, the temporal step size (e.g., time it takes to acquire the innermost radial angles in the KWIC filter) used to advance the sliding window is defined as the temporal resolution 504, and the entire length of the KWIC filter 500 is defined as the temporal footprint 506.

Figure 6:
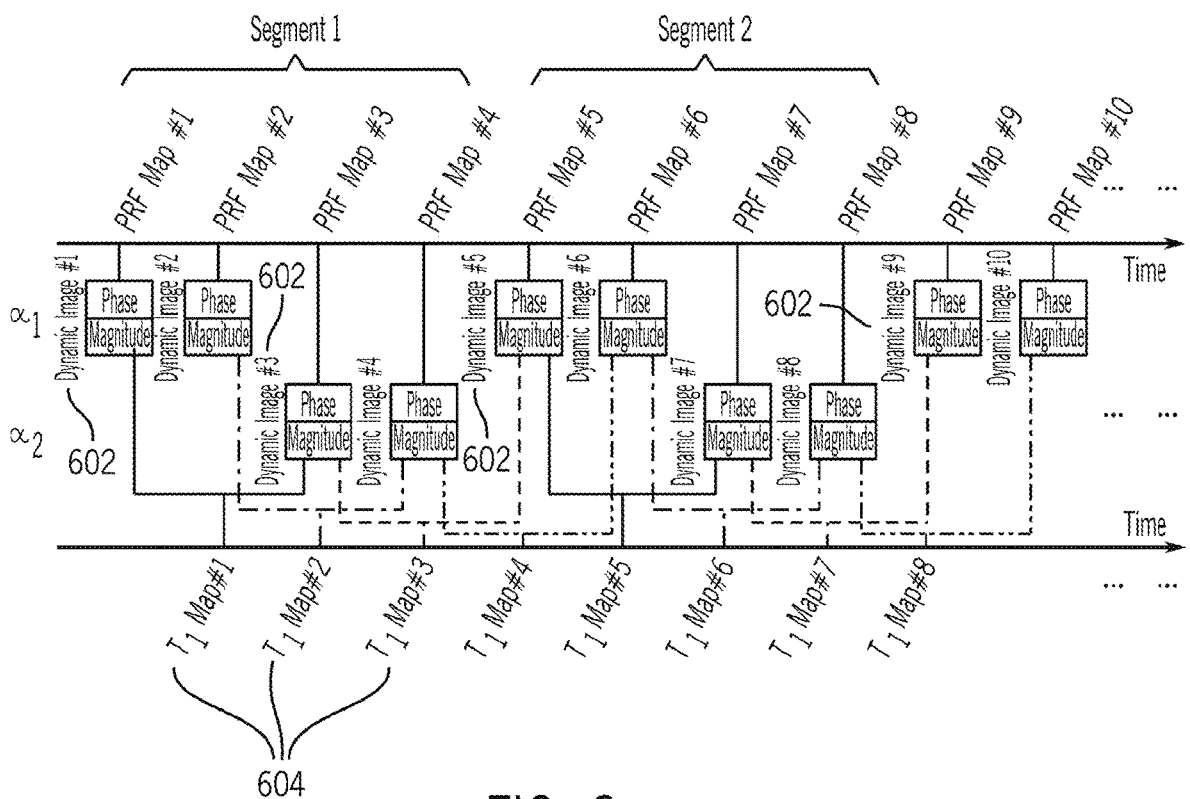
FIG. 6 illustrates a method for calculating PRF temperature change using dynamic images from multiple flip angles with respect to reference phase maps, as well as calculating $T_1$ maps using dynamic images in accordance with an embodiment.
Figure 7:
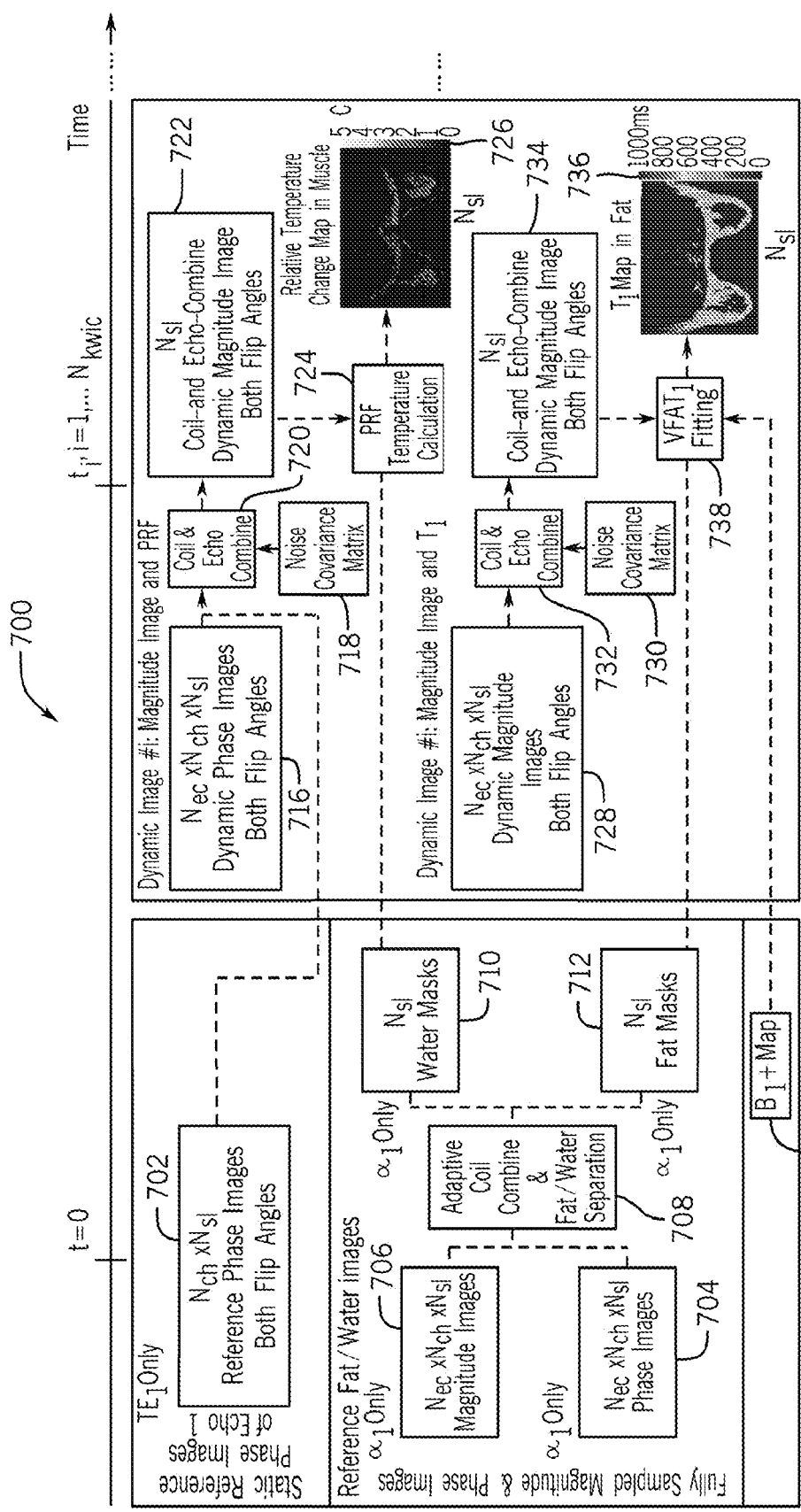
FIG. 7 illustrates a reconstruction process for $T_1$ and PRF temperature maps in accordance with an embodiment.

In an embodiment, a PRF temperature change may be calculated using dynamic images from both flip angles with respect to reference phase maps as shown in FIG. 6. A sliding-window approach is used to pair dynamic images 602 of different flip angles to calculate $T_1$ maps 604. FIG. 7 illustrates a reconstruction process for $T_1$ and PRF temperature maps in accordance with an embodiment. In this embodiment, the reconstruction process 700 for the VFA 3D stack-of-radial technique includes reconstructing static reference phase maps 702 at baseline temperature from all coil channels of the first echo using the same total number of radial spokes as that in the KWIC filter (500, shown in FIG. 5), but without the application of a KWIC filter. The reference phase maps 702, the noise covariance matrix 718 and dynamic phase images 716 (generated with the KWIC filter discussed above with respect to FIG. 5) are used for coil combination and echo combination 720 to produce coil- and echo-combined dynamic phase images 722 for both flip angles at a specified effective echo time TE≈$T_2$* (in an example, TE=10 ms), which represent the phase difference from the reference phase maps 702. The noise covariance matrix 730 and dynamic magnitude images 728 (generated with the KWIC filter discussed above with respect to FIG. 5) are used for coil combination and echo combination 732 to produce coil- and echo-combined dynamic magnitude images 734 for both flip angles.

For applications in mixed fat and water tissues, additional images may be reconstructed from a fully-sampled k-space dataset acquired at the baseline temperature with the smaller flip angle using adaptive coil combination. As shown in FIG. 7, water and fat maps 704, 706 and corresponding water and fat masks 710, 712 are reconstructed without using the k-space weighted image contrast (KWIC) filter. The reference water and fat maps include phase images 704 and magnitude images 706. Static water 710 and fat 712 masks may be calculated using a and an adaptive coil combination and fat-water separation algorithm 708 with a seven-peak fat spectral model and single effective $R_2$*. The water masks 710 and fat masks 712 may be used to determine the use of PRF or $T_1$ for temperature calculation in specific tissue types. For example, a PRF temperature calculation 724 is used for water voxels identified by the water mask 710 and a $T_1$ temperature calculation 738 for fat voxels identified by the fat mask 712. For the PRF temperature calculation, dynamic phase images (at time points ti) may be reconstructed using a KWIC filter (shown in FIG. 5) and for the $T_1$ temperature calculation, dynamic magnitude images 728 may be reconstructed using a KWIC filter (shown in FIG. 5). In aqueous tissues, for the dynamic phase images 716 the average phase of a region of interest (ROI) outside of the heated region may be used as a reference to correct for $B_0$ drift. In adipose tissues, fat dynamic magnitude images 728 of all echoes may be sum-of-squares combined for all flip angles to increase SNR.

Proton resonance frequency (PRF) temperature change 724 may be calculated using the phase component in aqueous tissues identified on the water mask 710. Specifically, PRF temperature change 724 may be calculated directly from the coil- and echo-combined dynamic phase images 722 as $$\Delta T(t) = -\frac{\Phi(t) - \Phi_{ref}(t)}{\alpha \cdot TE \cdot \gamma \cdot B_0}, \text{ with } TE = 10 \text{ ms.} \tag{3}$$

PRF temperature maps 726 from both flip angles may then be temporally interleaved to improve temporal resolution. VFA $T_1$ maps 736 are calculated using the magnitude component in adipose tissues identified on the fat mask 712. In an embodiment, prior to temperature mapping $B_1$+ field variation may be measured. The $B_1$+ map 714 and the coil-and-echo-combined dynamic magnitude images 734 may be used in a standard VFA fitting 738 procedure to produce $T_1$ maps 736 in fat compartments. To maintain consistent temporal resolution for dynamic $T_1$ mapping across the segmented acquisition of different flip angles, a sliding-window approach is used to pair images of different flip angles to calculate $T_1$ maps (as illustrated in FIG. 6).

Figure 8:
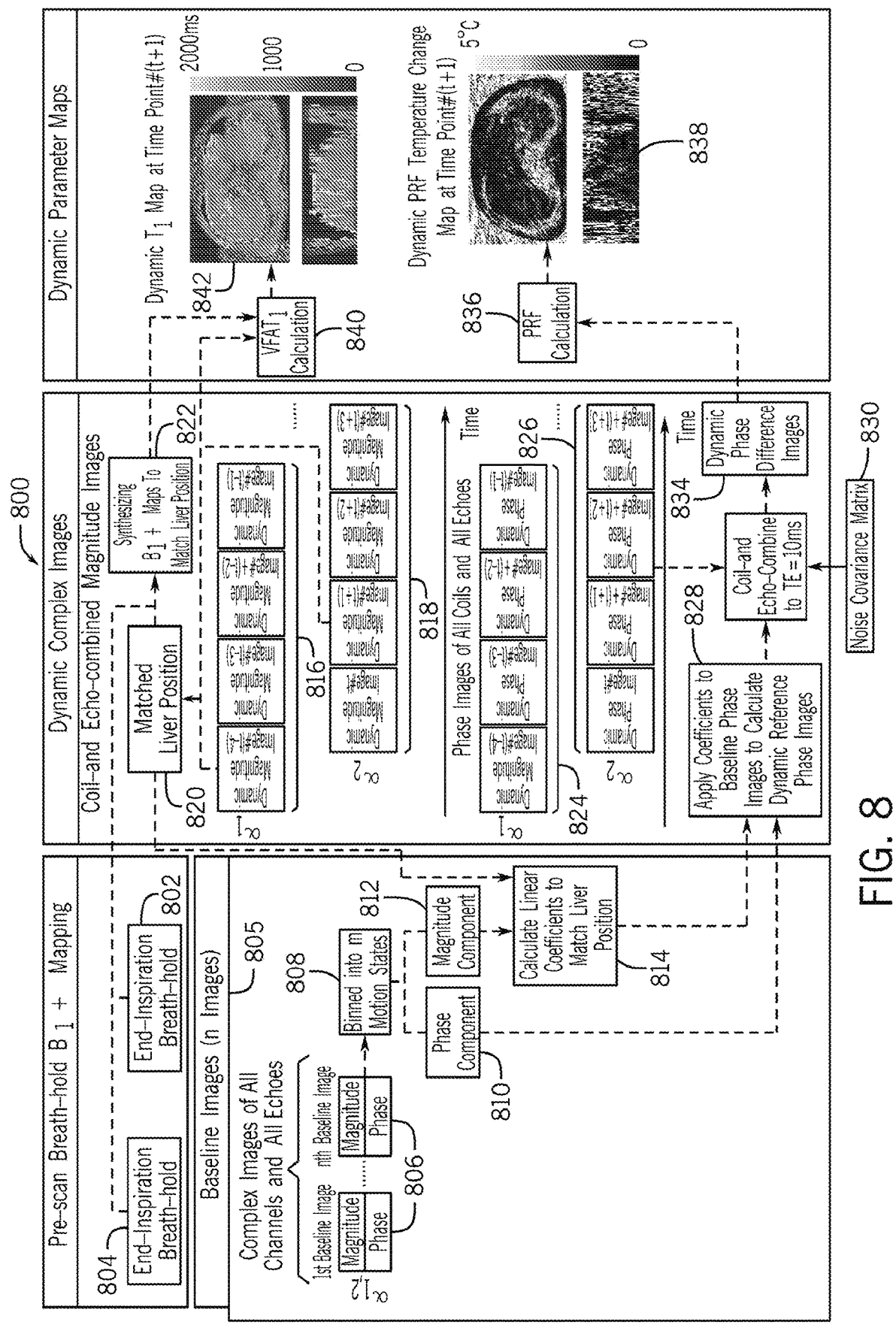
FIG. 8 illustrates a reconstruction process for $T_1$ and PRF temperature maps for a moving organ in accordance with an embodiment.

In another embodiment, the VFA 3D stack-of-radial technique may be adapted for simultaneous proton resonant frequency shift (PRF) and $T_1$-based thermometry in moving organs (e.g., the liver). Based on the movement of the anatomy during free-breathing, a thinner slice thickness may be used to improve temporal resolution. For example, the liver moves on average 13 mm during free breathing, which may require a thinner slice thickness of 3 mm. In addition, the number of slices and spatial resolution may be reduced to further improve temporal resolution below is in order to fully capture and resolve the respiration-induced motion. FIG. 8 illustrates a reconstruction process for $T_1$ and PRF temperature maps for a moving organ in accordance with an embodiment. In this reconstruction process 800, a baseline image library 805 may be formed using the first n images 806 reconstructed with KWIC method in FIG. 5 from data acquired using the radial VFA sequence prior to heating. In an embodiment, magnitude and phase images of the first 20 time points were grouped as a baseline library. The baseline image library 805 may be used to provide a baseline image for the KWIC reconstruction method for PRF temperature change calculation 836. To increase temporal resolution to resolve the motion of the liver during free-breathing, a backward-looking k-space weighted image contrast (KWIC) filter is applied to the raw k-space data to generate dynamic magnitude images 816, 818 for both flip angles and dynamic phase images 824, 826 from both flip angles. For each temporal point, the spokes acquired in the past are used to fill out the higher spatial frequency annuli of the filtered k-space. As discussed above with respect to FIG. 5, the KWIC filter is divided into several annuli and the number of radial angles in each annulus followed Fibonacci sequence. The time it takes to acquire all radial angles in a single KWIC filter is defined as the temporal footprint, while the time it takes to acquire the number of radial angles in the center of the KWIC filter is defined as temporal resolution. After regridding and Voronoi density compensation, complex images of individual channels and echoes may be obtained, using different techniques for magnitude and phase images as outlined below. The KWIC filter may then be moved forward in the temporal direction in a sliding window fashion by a step size that is equal to the number of radial angles in the center of the KWIC filter until all dynamic images are reconstructed.

The magnitude images of individual channels and echoes are then first coil-combined using a modified Roemer's equation with the noise covariance matrix and then echo-combined using sum-of-squares to enhance signal-to-noise ratio (SNR). As mentioned above, the magnitude images of the first 20 time points were grouped as a baseline library. To calculate dynamic $T_1$ maps, the rest of magnitude images 816 acquired with one flip angle are each paired to magnitude images 818 acquired with the other flip angle from a neighboring segment that had the highest structural similarity coefficients of the liver position. To compensate for the effect of $B_1+$ field inhomogeneities on the accuracy of $T_1$ measurements, two $B_1+$ maps 802,804 may be acquired during breath-holding with the liver at end-expiration and end-inspiration, respectively, prior to heating. A dynamic $B_1+$ map 822 is derived from the two end-expiration and end-inspiration $B_1+$ maps using linear interpolation to match the liver position 820 in each pair of dynamic VFA magnitude images to produce dynamic $T_1$ maps 842.

Figure 9:
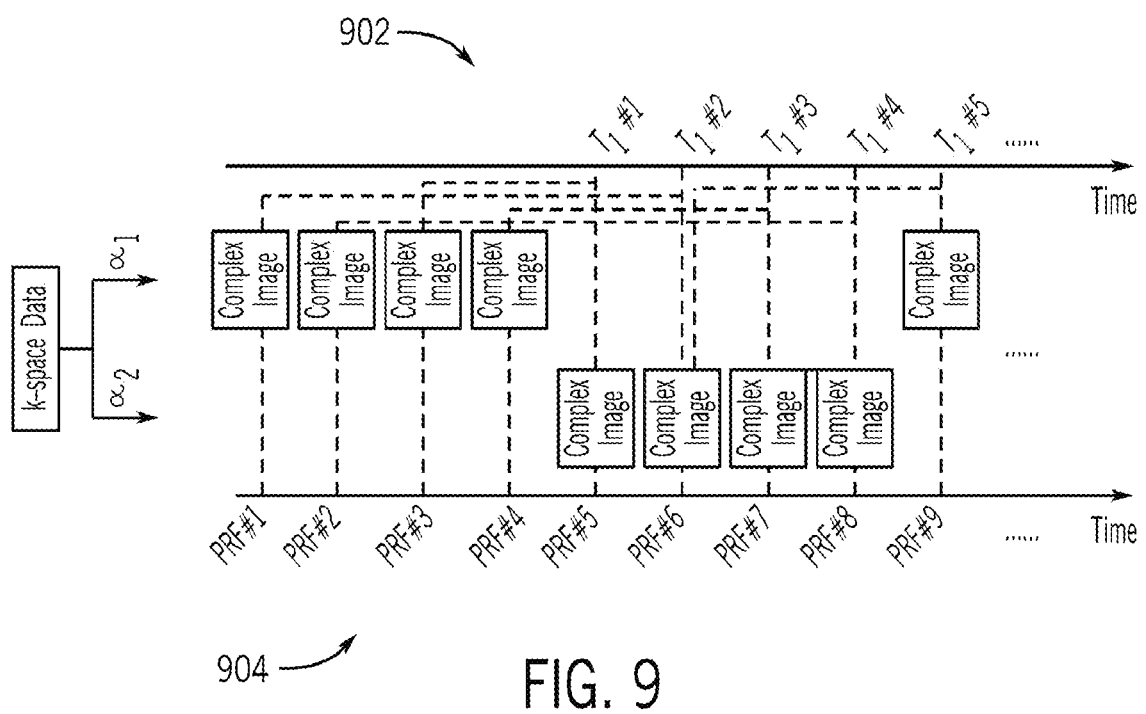
FIG. 9 illustrates a determination of the time stamps of $T_1$ and PRF maps fir a moving organ in accordance with an embodiment.

To calculate PRF relative temperature change 836, a modified multi-baseline approach is adopted during the coil- and echo-combination stage. In an embodiment, the magnitude images (e.g., 20) in the baseline library 805 are first binned into m (e.g., 4) distinct motion states 808 based on the liver position 820. For each new dynamic magnitude image, linear coefficients 814 are calculated so the combination of these binned baseline images best match the liver position in the dynamic image. These linear coefficients 814 are then applied to the corresponding binned baseline phase images 810 of individual channels and echoes to form a reference phase image 828, which along with the dynamic phase images 824, 826 and the noise covariance matrix 830 are inputs into the coil- and echo-combination algorithm 832, where the phase was unwrapped along the echo dimension and combined to a specified effective echo time (in an example TE=10 ms) with the output being a single phase image 834 representing the phase difference $\Delta\varphi$ between the baseline and dynamic time points. The PRF temperature change 836 at this time point thus may be readily calculated and a temperature change map 838 generated. The determination of the time stamps of $T_1$ and PRF maps is illustrated in FIG. 9. For $T_1$ 902, its dynamic time point may set to be the same as that of the later magnitude image of the pair that was used for its calculation. For PRF 904, it was more straightforward as phase components of dynamic complex images acquired with both flip angles were interleaved to establish a steady stream of PRF relative temperature change maps.

Figure 10:
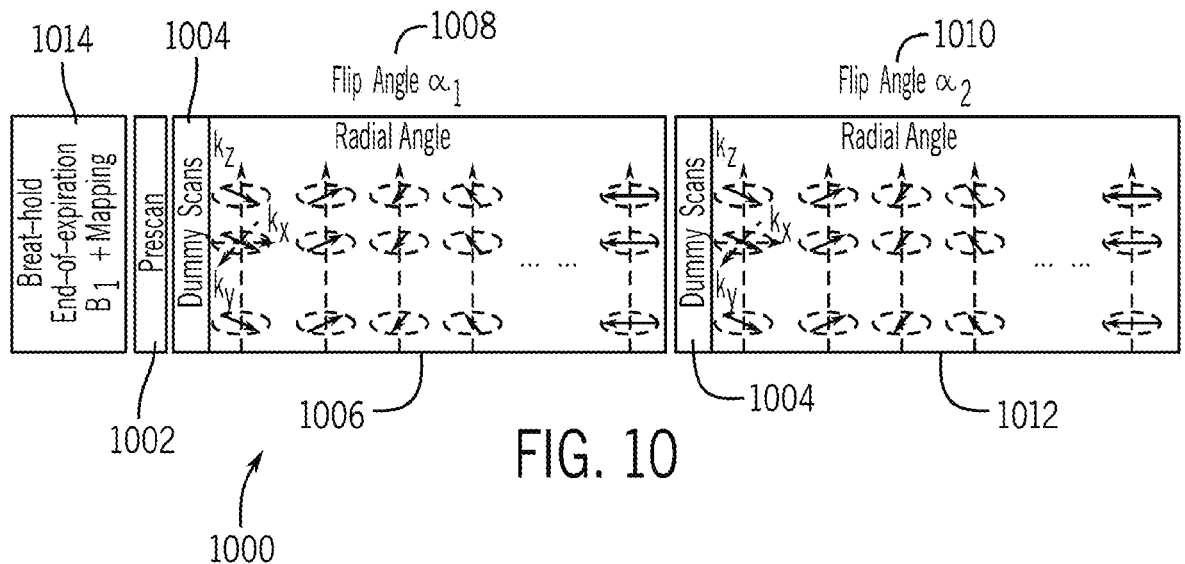
FIG. 10 a variable flip angle (VFA) golden-angle (GA) ordered 3D stack-of-radial MRI technique for quantitative parameter mapping in accordance with an embodiment.

As mentioned, in another embodiment, the VFA 3D stack-of-radial technique ("radial VFA") may be used to perform simultaneous quantification of proton-density fat fraction (PDFF), $R_2^*$, and $T_1$ during a free-breathing acquisition, e.g., in the liver. FIG. 10 a variable flip angle (VFA) golden-angle (GA) ordered 3D stack-of-radial MRI technique for quantitative parameter mapping in accordance with an embodiment. The VFA multi-echo gradient echo 3D stack-of-radial sequence ("radial VFA") 1000 uses radial sampling in the $k_x$-$k_y$ plane and Cartesian encoding along $k_z$. Radial VFA scans may be performed in the axial orientation, with the z axis aligned to the superior-inferior direction of the subjects. In FIG. 8, the entire k-space data set (and prescribed radial angles) acquired in a first segment 1006 at a first flip angle 1008. The entire k-space data set is then acquired in a second segment 1012 at a second flip angle 1010. For each segment 1006, 1012, all $k_z$ partitions may first be acquired with multi-echo gradient echo readouts using the same radial angle, and the radial angle increased by the golden angle ($\theta_G$=111.246°) until the prescribed number of radial readouts is acquired. While FIG. 10 illustrates the use of two flip angles $\alpha_1$ 1008 and $\alpha_2$ 1010, it should be understood that in other embodiments other numbers of different flip angles may be used. In an embodiment, the two flip angles were optimized for $T_1$ of 300-1200 ms in the liver at 3T using the VFA 3D stack-of-radial technique such that they generated 71% of the signal intensity of the Ernst angle. Dummy scans 1004 (spokes with radial angle of 0°) are performed between flip angles (e.g., $\alpha_1$ 1008 and $\alpha_2$ 1010) to establish steady state for the spoiled gradient-echo signal at a particular flip angle. The dummy scans 1004 are not used for image reconstruction. In an embodiment, a prescan 302 including additional readouts with radial angles of 0°, 90°, 180° and 270° is acquired at the beginning of the scan to calibrate shifts of k-space readouts due to gradient delays and eddy currents and correct the data to compensate for these effects. $B_1+$ maps 1014 may also be acquired in a pre-scan during breath-hold at end-of-expiration.

Figure 11:
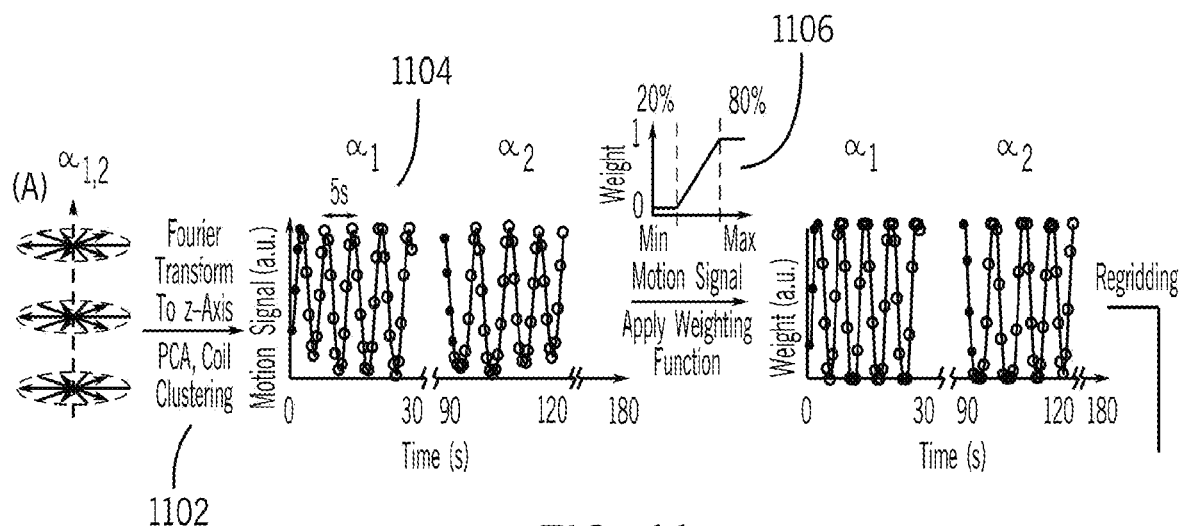
FIG. 11 illustrates an example method for extraction of a motion signal and application of soft-gating to reconstruct end-of-expiration images in accordance with an embodiment.

The acquired radial VFA MR data is processed for reconstruction. First, readouts with the same radial angle may be collected along the $k_z$-axis, and their $(k_x,k_y)=0$ points are Fourier-transformed to obtain projection profiles in z for all channels, which captures motion for both flip angles. FIG. 11 illustrates and example method for extraction of a motion signal and application of soft-gating to reconstruct end-of-expiration images in accordance with an embodiment. Principal component analysis (PCA) 1102 may then be performed to extract the first two principal components, and channels exhibiting similar results (in an example, 95% correlation threshold) may be clustered to generate a motion navigation signal 1104. In an embodiment, a weighting function 1106 from 0 to 1 may then be applied to the signal whose amplitudes ranged between 20% and 80% of the maximum, while those above and below were assigned a weighting of 1 and 0, respectively, as shown in FIG. 11. These weightings are applied to radial data, i.e. soft gating, and the radial data is then re-gridded and channel-combined to produce complex images with the liver at end-expiration. Magnitude images of all echoes may be combined via sum-of-squares for VFA $T_1$ calculation in combination with the $B_1+$ maps acquired in a pre-scan during breath-hold at end-of-expiration. PDFF and $R_2^*$ may be calculated with the complex multi-echo images acquired with the smaller flip angle to minimize $T_1$ bias, using a seven-peak fat model and single effective $R_2^*$ per voxel.

As mentioned, the radial VFA technique described herein may be used for temperature mapping. The radial VFA technique measures actual $T_1$ values, which could provide advantages in certain applications by eliminating the need for a baseline image and reducing $T_1$ errors caused by possible mismatch between baseline and dynamic images. The potential variation in temporal resolution when advancing the KWIC filter across segments and flip angles in the proposed radial VFA technique was largely addressed by adopting a sliding-window pairing of different flip angles for $T_1$ fitting.

The radial VFA acquisition and reconstruction parameters used in the examples discussed herein were chosen to strike a balance between temporal resolution and temperature measurement accuracy/stability (mainly dictated by SNR). Depending on the application, parameters of a radial VFA sequence can be adjusted to achieve specific needs. For example, to monitor a smaller region, the number of slices or slice thickness could be reduced, which would further enhance temporal or spatial resolution. In an example, 36 radial angles (including dummy TRs) per segment setup resulted in a 6-10 s overall temporal footprint for each pair of images acquired with both flip angles to produce dynamic $T_1$ maps. When applied to targets with a greater degree of motion such as the liver, the number of radial angles in a single segment may be reduced to improve the temporal resolution and/or footprint. Alternatively, the through-plane dimension may be divided into multiple slabs. However, these solutions would come at the penalty of increasing the ratio of dummy scans. Another solution is to divide the acquisition along the through-plane dimension into segments as well and to loop through all flip angles within each segment before moving on to the next in order to reduce such overall temporal footprint without increasing scanning time.

In various embodiments, additional techniques may be used for improving the proposed radial VFA technique. Since each spoke in the stack-of-radial acquisition samples the center of k-space, in an embodiment the same acquisition can be used as self-navigator signals and support motion compensation algorithms to further improve motion robustness. The self-navigator signal can be extracted from the magnitude of the central k-space points of each radial spoke at $k_z=0$ or multiple $k_z$ locations, and a subset of coils that were close to the moving target. As $B_1+$ maps are generally acquired with breath-holding (e.g. at the end of expiration), the self-navigator signal can be used to choose radial spokes that were also acquired at the end of expiration to make the proposed radial VFA technique more suitable for temperature mapping in organs that experience greater levels of motion, such as the liver. Resulting undersampling can be compensated for by adopting the KWIC filter reconstruction where the center of the filter is filled out by radial spokes acquired at the end of expiration and the periphery radial spokes acquired during other breathing stages. Soft gating where each radial spoke is weighted by the strength of its corresponding self-navigator signal (compared to a reference) can also be used which could generate true phase maps for water/fat separation.

In another embodiment, rotating the radial spokes along the through-plane direction also in a GA-ordered fashion may be used to suppress streaking artifacts caused by undersampling. This can be used to reduce the necessary number of spokes in a KWIC filter and improve temporal resolution and/or footprint. In an embodiment, a simultaneous multi-slice or multi-slab imaging technique is another way to accelerate acquisition speed. In other embodiments, in lieu of a KWIC filter, phase-sensitive parallel imaging, compressed sensing and other reconstruction techniques for undersampled data can be employed to reduce temporal footprint. In another embodiment, the low-rank nature of phase change along the temporal dimension during HIFU heating and the sparsity of the change in complex dynamic images can be combined to reconstruct images from highly undersampled k-space data to achieve high temporal resolution of both PRF temperature change and $T_1$ maps. In another embodiment, the proposed radial VFA sequence may be used to evaluate $T_1$ pre-contrast as well as $T_1$ change after the injection of contrast agents. In yet another embodiment, other temperature-dependent MR parameters such as magnetization ($dM_0/dT \approx -0.3\%/°$ C.) as a by-product of $T_1$ fitting and to a lesser degree the $R_2^*$ relaxation time from the multi-echo data can also be used in combination with PRF and $T_1$ to improve temperature measurement accuracy. Lastly, considerable computational time may be required for coil combination and $T_1$ fitting. In an embodiment, the computational efficiency of the reconstruction pipeline may be improved to enable real-time monitoring of thermal therapy and feedback control.

The following examples set forth, in detail, ways in which the present disclosure was evaluated and ways in which the present disclosure may be used or implemented, and will enable one of ordinary skill in the art to more readily understand the principles thereof. The following examples are presented by way of illustration and are not meant to be limiting in any way.

Example 1

In various example studies discussed below, the accuracy of the disclosed VFA 3D stack-of-radial technique for $T_1$ quantification was evaluated in a reference $T_1/T_2$ phantom. In vivo non-heating experiments were conducted in healthy subjects to evaluate the stability of PRF and $T_1$ in the brain, prostate, and breast. In addition, the proposed VFA 3D stack-of-radial technique was used to monitor high intensity focused ultrasound (HIFU) ablation in ex vivo porcine fat/muscle tissues and compared to temperature probe readings.

In this example, the VFA 3D stack-of-radial technique achieved 3D coverage with 1.1×1.1 to 1.3×1.3 mm² in-plane resolution and 2-5 s temporal resolution. During 20-30 minutes of non-heating in vivo scans, the temporal coefficient of variation for $T_1$ was <5% in the brain, prostate, and breast fatty tissues, while the standard deviation of relative PRF temperature change was within 3° C. in aqueous tissues. During ex vivo HIFU ablation, the temperatures measured by PRF and $T_1$ were consistent with temperature probe readings, with an absolute mean difference within 2° C.

In this example study, to evaluate the accuracy of $T_1$ measurements the proposed VFA 3D stack-of-radial technique ("radial VFA") was compared to reference 2D Cartesian inversion recovery (IR) and 3D Cartesian VFA techniques in a reference $T_1/T_2$ phantom, which contained 14 samples with $T_1$ ranging from 50 to 2500 ms. In the examples, all scans were performed on a 3 T MRI scanner with a body array coil and a spine array coil. The phantom was first placed inside the scanner bore for one hour to achieve thermal equilibrium at 21° C. Parameters for radial VFA were: axial slices, FOV=256×256×48 mm³, matrix size=224×224×16, 6 echoes, TE$_1$/ΔTE=1.51/1.36 ms, TR=10.34 ms, flip angles=2°, 22°, 43° (targeted T$_1$ range 100-2000 ms), bandwidth=1150 Hz/pixel; for 2D Cartesian IR:FOV=256×256×48 mm$^3$, matrix size=256×256×16, TE=13 ms, TR=8000 ms, inversion time (TI)=50, 100, 200, 300, 500, 750, 1000, 1500, 2500 ms, bandwidth=450 Hz/pixel; for 3D Cartesian VFA:FOV=256×256×48 mm$^3$, matrix size=256×256×16, 6 echoes, TE$_1$/ΔTE=1.43/1.41 ms, TR=10.4 ms, flip angles=2°, 22°, 43°, bandwidth=1150 Hz/pixel.

Figure 12A:
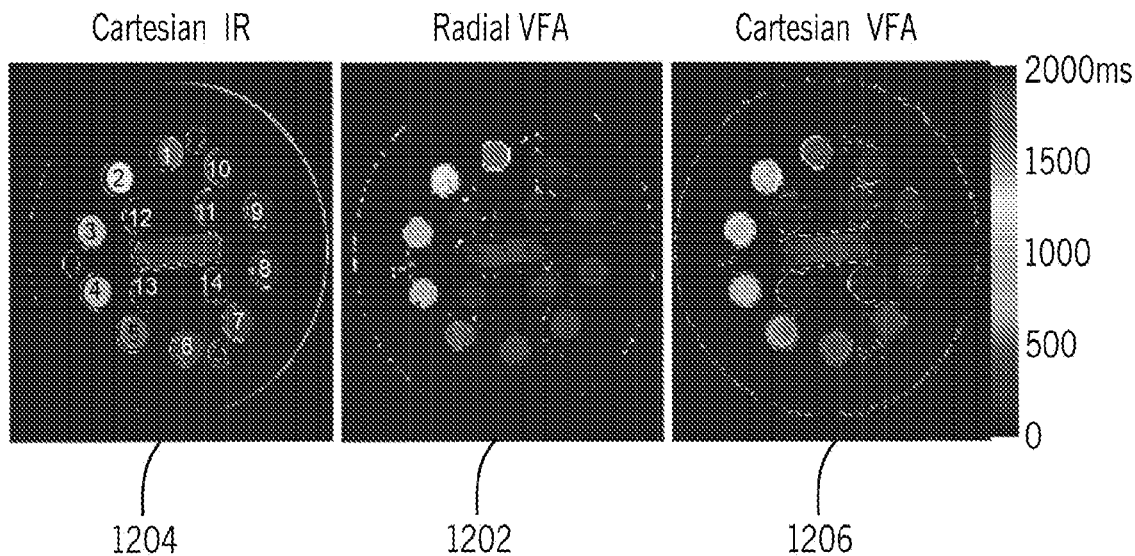
FIG. 12A shows example $T_1$ maps acquired using a VFA 3D stack-of-radial technique compared to standard 2D Cartesian inversion-recovery (IR) and 3D Cartesian VFA protocols in a $T_1/T_2$ phantom in accordance with an embodiment.
Figure 12B:
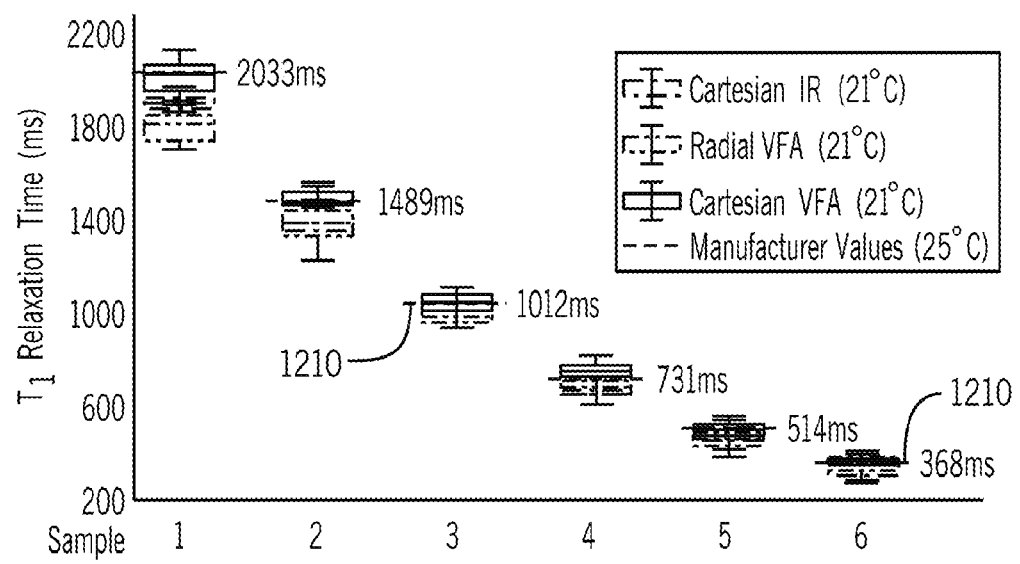
FIG. 12B shows an example box plot showing the agreement between the three protocols shown in FIG. 12A in the six samples with $T_1$ values (300-2000 ms) that are representative of tissues of interest (e.g., brain, prostate, breast) in accordance with an embodiment.

FIGS. 12A-12B show an example evaluation of T$_1$ mapping using the VFA 3D stack-of-radial MRI technique in a phantom in accordance with an embodiment. Example T$_1$ maps produced by the proposed radial VFA 1202, 2D Cartesian IR 1204, and 3D Cartesian VFA 1206 techniques for the standard T$_1$/T$_2$ phantom are shown in FIG. 12A. Because of the different pulse sequence constraints on the 3D gradient-echo sequences compared to the 2D IR sequence on the scanner in this example, radial and Cartesian VFA protocols had the same slightly lower in-plan spatial resolution than the 32D Cartesian IR protocol. All other parameters were matched between the three protocols. FIG. 12B shows a box plot 1208 comparing the three protocols in six compartments that had T$_1$ values representative of those encountered in the brain, prostate, and breast. The manufacturer-provided T$_1$ values at 25° C. are included as dashed black lines 1210. However, in this example, the ambient temperature during the scan was 21° C. Compared to the reference Cartesian IR measurements, radial VFA T$_1$ had relative differences of 3.5-8% and Cartesian VFA T$_1$ had relative differences of 6-10%. This demonstrates that T$_1$ mapping using the proposed radial VFA method is consistent with Cartesian IR and performs slightly better than Cartesian VFA. Radial VFA T$_1$ values demonstrated good agreement with Cartesian IR measurements.

In another example study, a total of fourteen healthy subjects were studied during non-heating MRI scans without breath-holding on a 3T scanner to evaluate the proposed radial VFA sequence, in particular, to assess the stability of the radial VFA sequence for PRF and T$_1$ mapping under the potential influence of different sources of motion. Targeted organs included brain (n=1, male), prostate (n=5, all males) and breast (n=8, all females). Fat/water separation was only performed for breast datasets. To quantify the stability of T$_1$ measured in human subjects during a 20-30-minute scan, the temporal coefficient of variation (COV) was calculated on a voxel-by-voxel basis by dividing the temporal standard deviation of T$_1$ during the entire scan by its mean. The stability of PRF temperature measurements was assessed by measuring the temporal mean and standard deviation (SD).

The scanning parameters for the example in vivo non-heating brain scan were: Field of View (FOV) 300×300×160 mm$^3$, matrix size 256×256×32, resolution 1.17×1.17×5 mm$^3$, slice orientation axial, RF coils and channels (in addition to spine 12) were head/neck 64, flip angles 3° and 33°, targeted T$_1$ range 300~1500 ms, number of echoes/TE$_1$/ΔTE 6/1.56/1.31 ms, TR 9.43 ms, number of segments 96, total running time 34.8 minutes, number of radial spokes in center/in total of KWIC filter 8/233, temporal resolution/temporal footprint of dynamic images 4.8/140.6. The scanning parameters for the example in vivo non-heating prostate scan were: Field of View (FOV) 380×380×90 mm$^3$, matrix size 288×288×18, resolution 1.32×1.32×5 mm$^3$, slice orientation axial, RF coils and channels (in addition to spine 12) were body 18, flip angles 2° and 15°, targeted T$_1$ range 1000~2000 ms, number of echoes/TE$_1$/ΔTE 6/1.41/1.52 ms, TR 9.19 ms, number of segments 64, total running time 16.7 minutes, number of radial spokes in center/in total of KWIC filter 8/233, temporal resolution/temporal footprint of dynamic images 2.6/77.1 s. The scanning parameters for the example in vivo non-heating breast scan were: Field of View (FOV) 350×350×120 mm$^3$, matrix size 288×288×24, resolution 1.21×1.21×5 mm$^3$, slice orientation coronal, RF coils and channels (in addition to spine 12) were breast 18, flip angles 5° and 27°, targeted T$_1$ range 300600 ms, number of echoes/TE$_1$/ΔTE 6/1.53/1.31 ms, TR 10.22 ms, number of segments 64, total running time 18.9 minutes, number of radial spokes in center/in total of KWIC filter 8/233, temporal resolution/temporal footprint of dynamic images 3.9/114.3. All studies were performed at 3 T. No partial Fourier along the slice dimension nor asymmetric echo along the readout dimension were used.

Figure 13A:
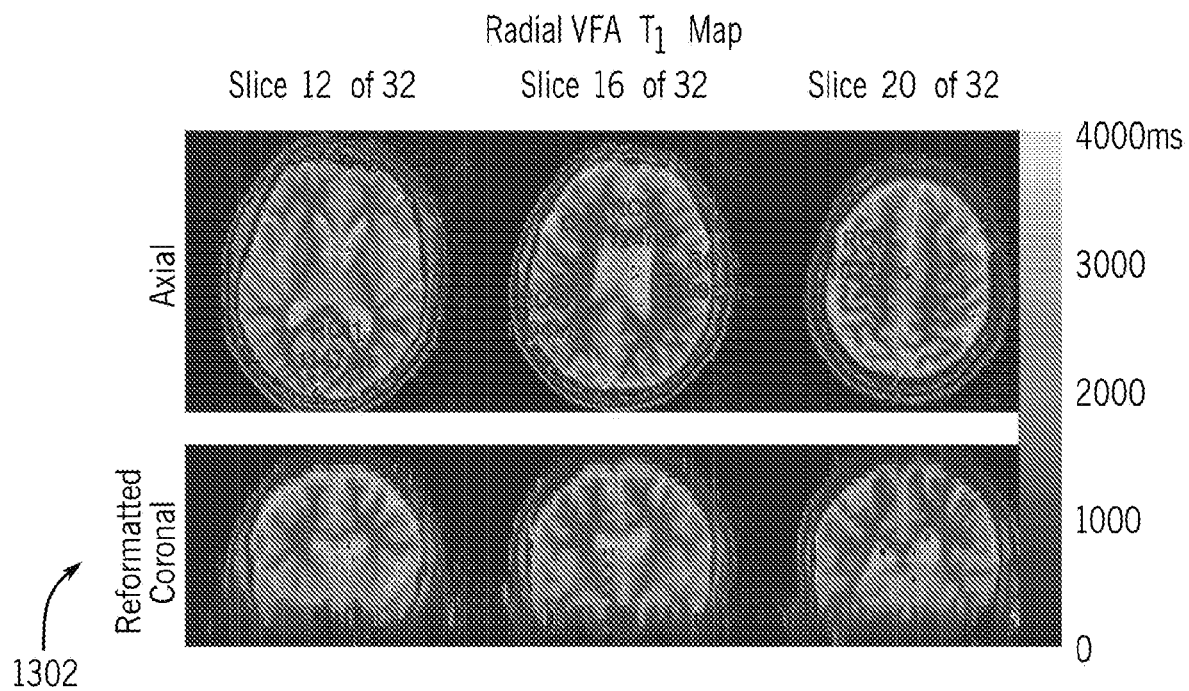
FIG. 13A shows example $T_1$ maps acquired in human brain using the variable flip angle 3D stack-of-radial technique during an example 35-minute non-heating scan in both prescribed axial and reformatted coronal slices in accordance with an embodiment.
Figure 13B:
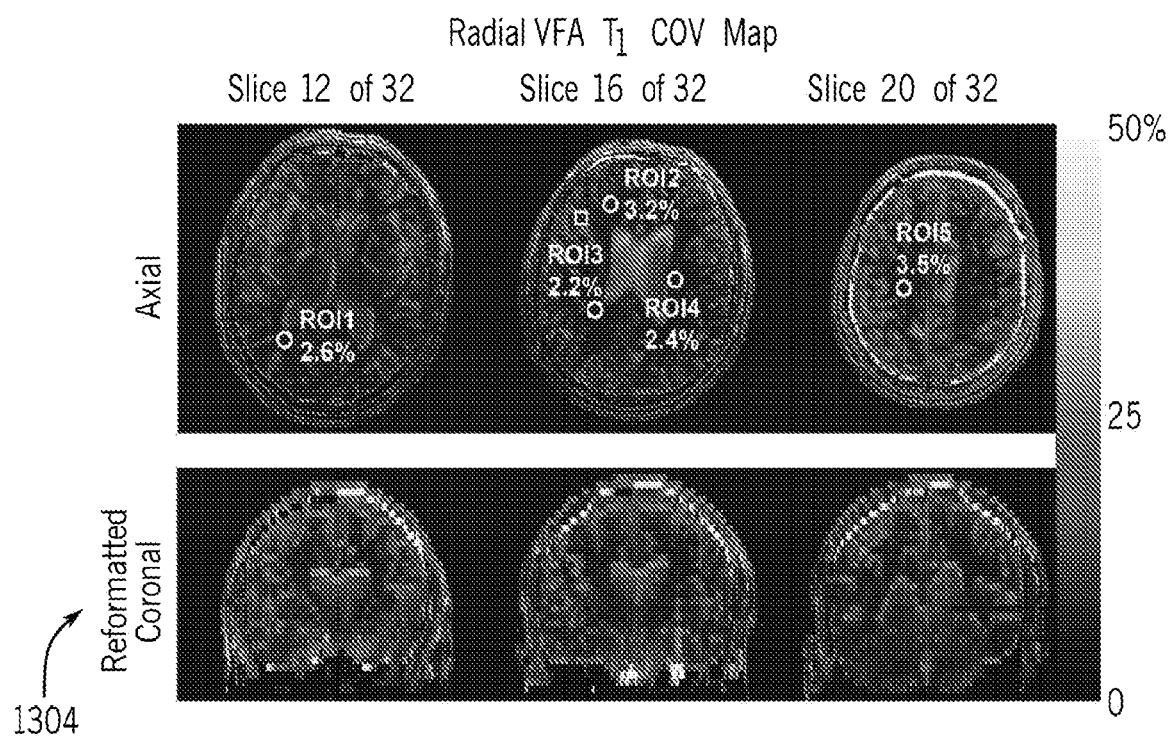
FIG. 13B shows example temporal coefficient of variation (COV) maps of $T_1$ of the same slices in FIG. 13A in accordance with an embodiment.
Figure 13C:
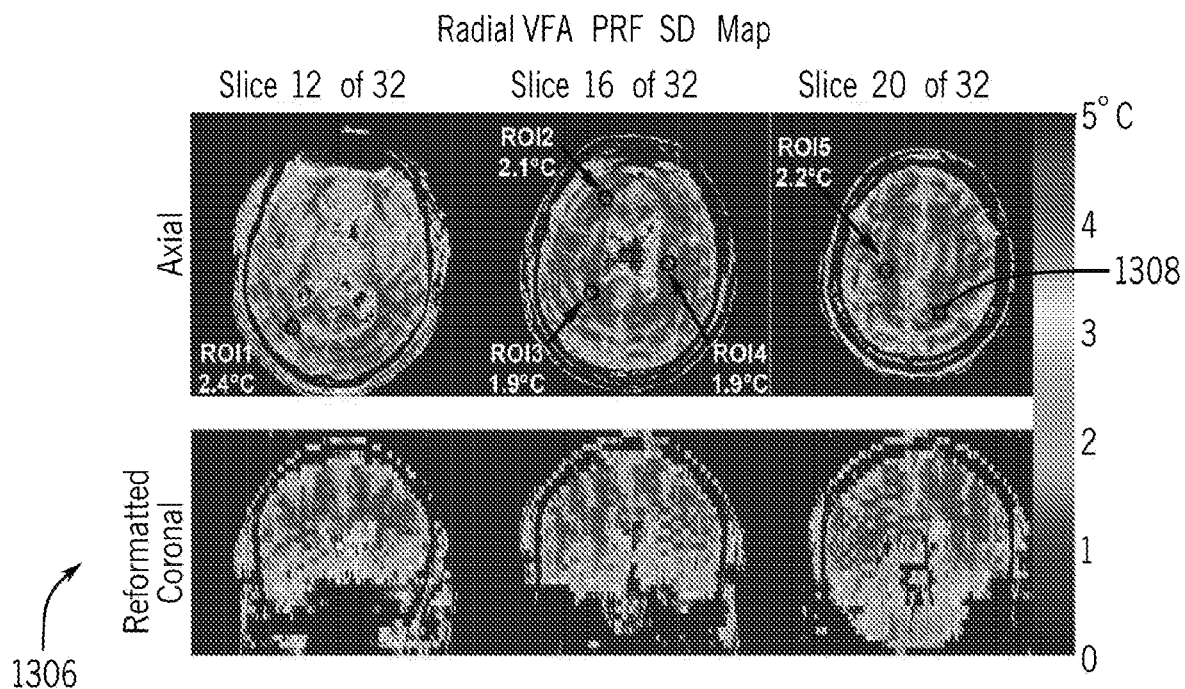
FIG. 13C shows example temporal standard deviation (SD) maps of proton resonant frequency shift (PRF) temperature change after $B_0$ field drift correction throughout the entire scan in accordance with an embodiment.

FIGS. 13A-13C show results from the example non-heating in vivo brain study. FIG. 13A shows the T$_1$ maps 1302 acquired in the brain using the radial VFA technique in the axial and reformatted coronal slice orientations. The corresponding T$_1$ COV maps 1304 for the radial VFA technique are presented in FIG. 13B. As shown in FIG. 13B, the radial VFA technique achieved full brain coverage with a temporal resolution of 4.8 s. In this example, white matter had the lowest T$_1$ COV, as the flip angles were optimized for this tissue. T$_1$ COV in gray matter and cerebrospinal fluid (CSF) were higher than that in white matter. In an evaluation of an embodiment, a total of 50 regions of interest (ROIs) of 9 voxels in size were drawn in the white matter across multiple slices to calculate the average T$_1$ and T$_1$ COV (as shown in FIGS. 13A and 13B). The T$_1$ measurements were stable over time, with the COV below 5% during the 35-minute scan despite potential motion. FIG. 13C shows the standard deviation (SD) 1306 of PRF temperature change throughout the entire scan after B$_0$ drift correction using a reference region 1308, which was below 3° C. in the majority of the brain.

Figure 14A:
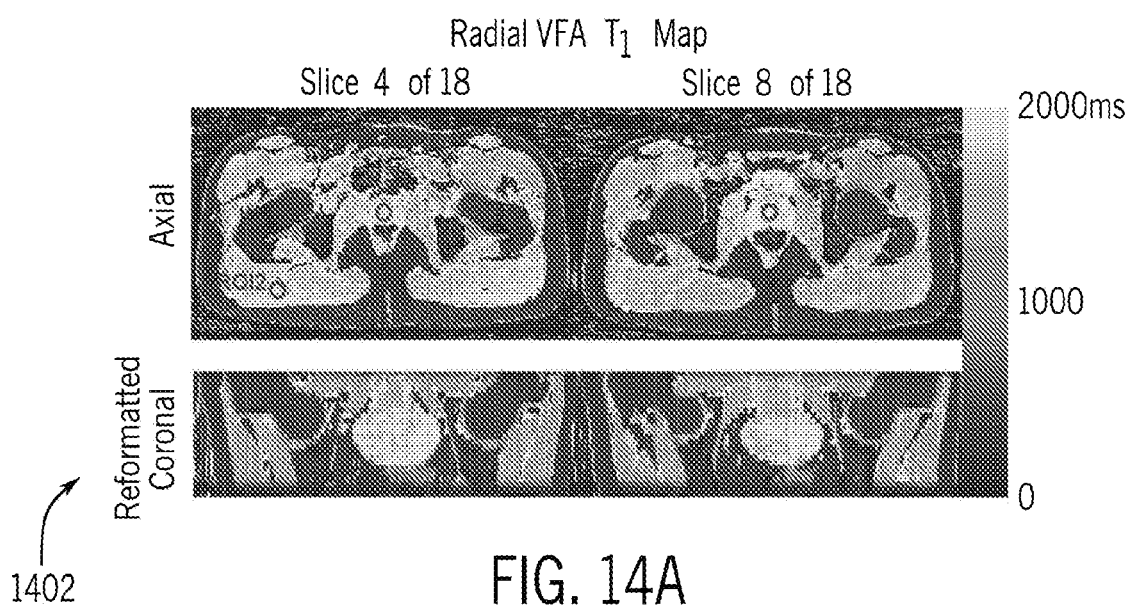
FIG. 14A shows example $T_1$ maps acquired in human prostate using the variable flip angle 3D stack-of-radial technique during a 17-minute non-heating scan in both prescribed axial and reformatted coronal slices in accordance with an embodiment.
Figure 14B:
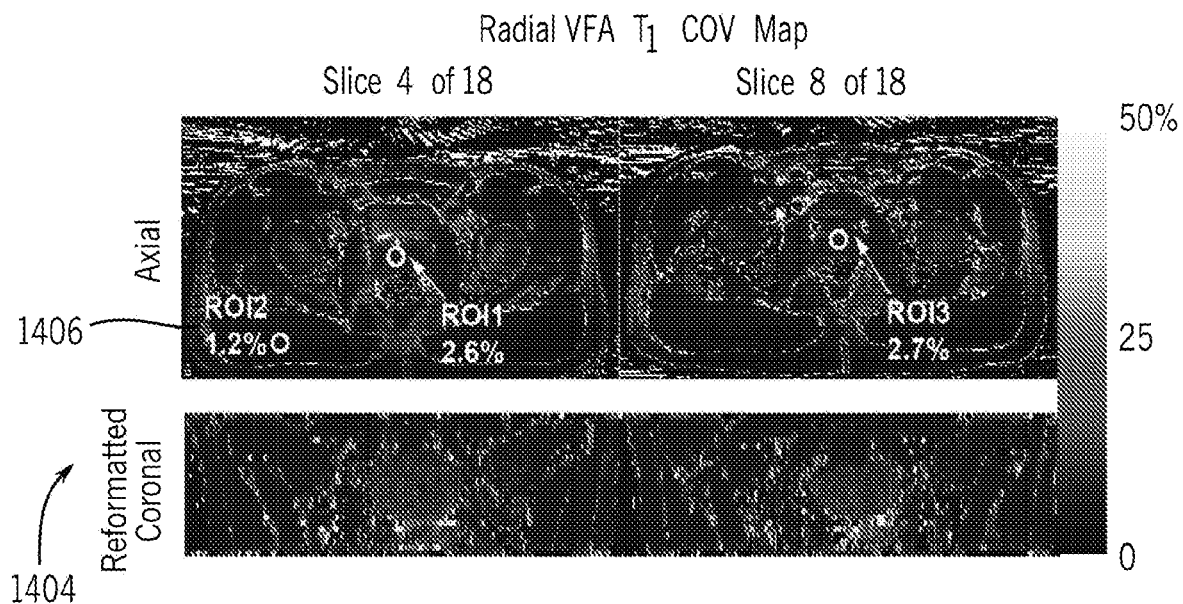
FIG. 14B shows example temporal coefficient of variation (COV) maps of $T_1$ in the same slices as FIG. 14A in accordance with an embodiment.
Figure 14C:
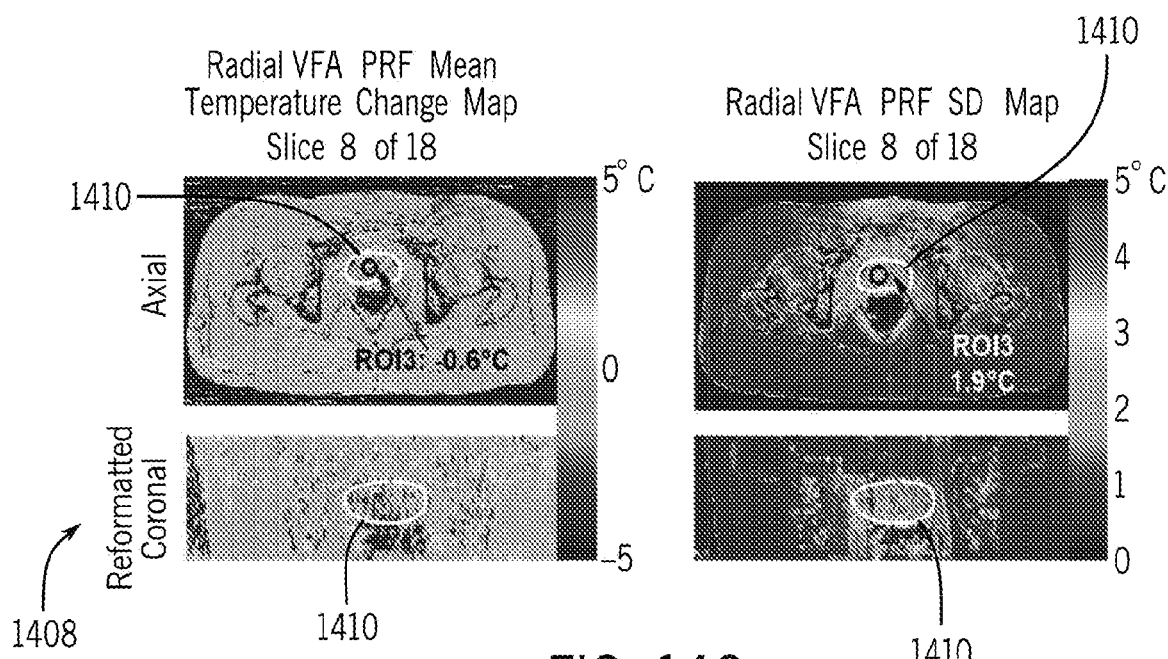
FIG. 14C shows the example mean proton resonant frequency shift (PRF) temperature change and standard deviation (SD) maps after $B_0$ field drift correction throughout the entire scan in accordance with an embodiment.

FIGS. 14A-14C show representative results from the example non-heating in vivo prostate study. In particular, FIGS. 14A-14C show representative pelvic T$_1$ 1402 and T$_1$ COV 1404 maps acquired from a male subject, both in the prescribed axial and reformatted coronal slice orientations. In this example, the proposed radial VFA sequence covered the entire prostate with a temporal resolution of 2.6 s. ROIs of 9 voxels in size were drawn inside the prostate across all slices to measure the T$_1$ COV. PRF temperature change over the entire course of the 35-minute scan caused by B$_0$ field drift was corrected by using the phase of surrounding muscle tissue as a reference (ROI2 1406 in FIG. 14B). FIG. 14C shows that the standard deviation (SD) 1408 of PRF temperature change after field drift correction was below 3° C. in the prostate. In this example study, inter-subject consistency of the radial VFA sequence was also assessed. A total of 120 ROIs of 9 voxels in size were drawn in the prostates of all five subjects, and the T$_1$ COV mean±SD of the per subject means was 2.2±0.9%, despite potential respiratory and peristaltic motion during the long free-breathing scans. PRF temperature change after field drift correction in these prostate ROIs yielded a mean±SD of the per subject means of −0.6±1.8° C. among the five subjects. The reference region for field drift correction is represented by ROI2 1406 in FIG. 14B and the prostate is outlined by contour 1410.

Figure 15A:
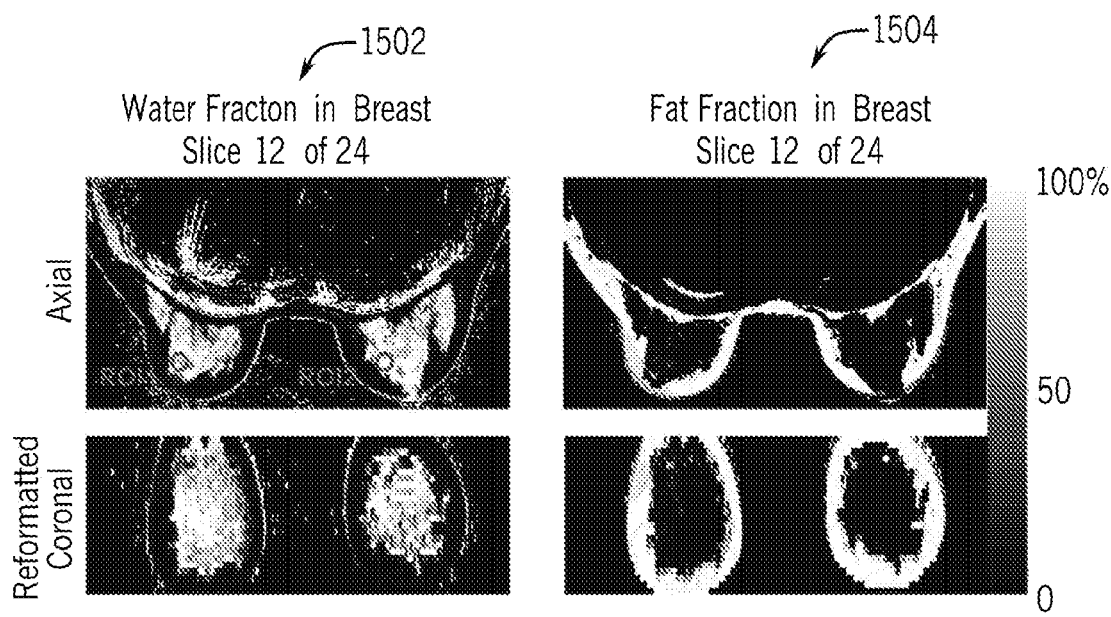
FIG. 15A shows example water and fat fraction maps acquired in human breasts using the variable flip angle 3D stack-of-radial technique at the beginning of the 19-minute non-heating scan in both prescribed axial and reformatted coronal slices in accordance with an embodiment.
Figure 15B:
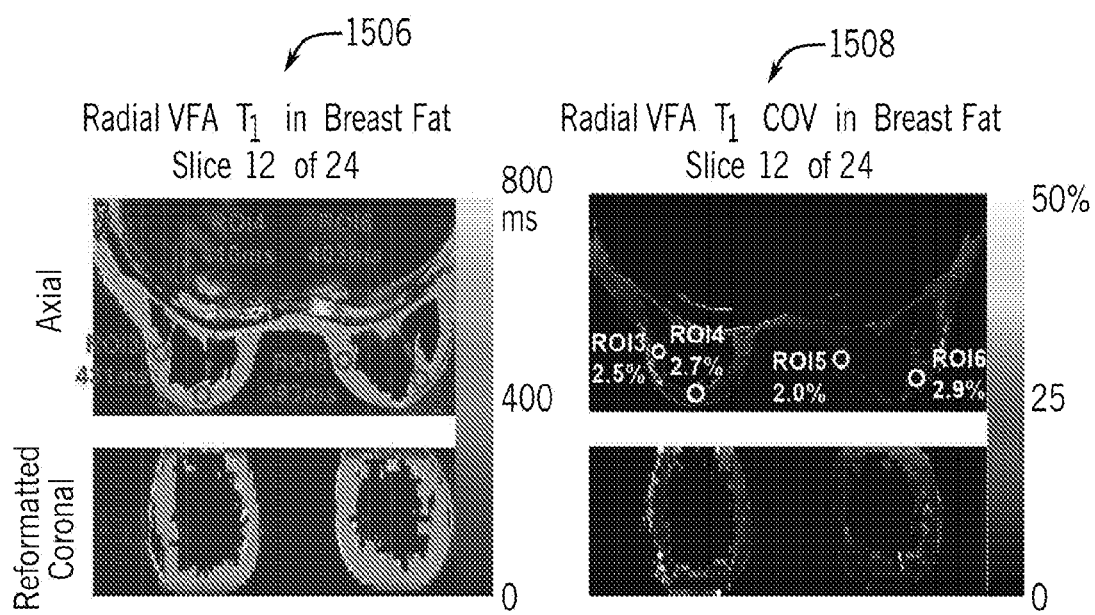
FIG. 15B shows example $T_1$ and its temporal coefficient of variation (COV) maps of the same slices of FIG. 15A in fatty tissues in accordance with an embodiment.
Figure 15C:
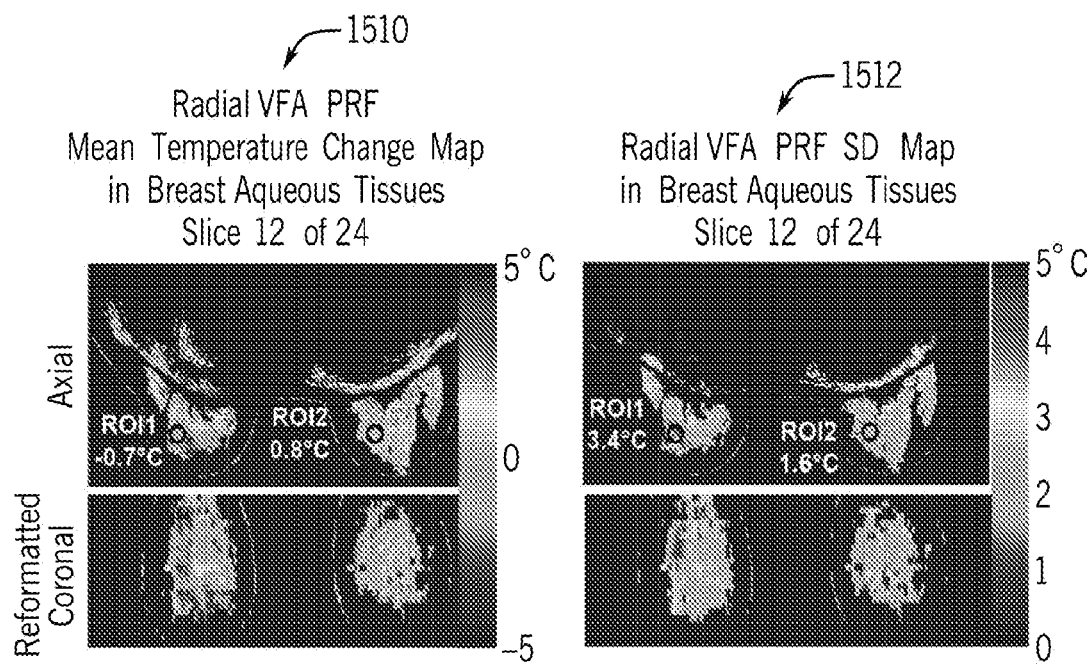
FIG. 15C shows example mean proton resonant frequency shift (PRF) temperature change and standard deviation (SD) maps in the aqueous tissues after $B_0$ field drift correction throughout the entire scan in accordance with an embodiment.

FIGS. 15A-15C show representative results from the example non-heating in vivo breast study. For breast scans of eight female subjects, fat-water separation was first performed in a reference frame. FIG. 15A shows representative quantitative water 1502 and fat 1504 fraction maps of the central slice from one subject in both the prescribed axial and reformatted coronal slice orientations. In this example, two representative ROIs of 9 voxels in size were drawn in the mammary gland (corresponding to regions with high water fraction). In predominantly fat voxels that had fat fraction >80%, $T_1$ 1506 and $T_1$ COV 1508 were calculated as shown in FIG. 15B. The radial VFA sequence offered full coverage of the breasts with a temporal resolution of 3.9 s. In voxels with a water fraction >80%, standard deviation (SD) 1512 of PRF temperature change is shown in FIG. 15C after $B_0$ field drift correction. Similar to prostate experiments, inter-subject analysis was conducted where 400 ROIs of 9 voxels in size were drawn in the breast fatty tissues and a $T_1$ COV mean±SD of the per subject means of 3.3±0.6% was calculated among the eight subjects. Mean PRF temperature change 1510 was found to be 0.7±2.2° C. inside another 200 ROIs in the mammary glands. The reference region for field drift correction was on a different slice and is not shown.

In another example, the ability of both PRF and $T_1$ mapping offered by the radial VFA technique to measure temperature change was evaluated during 3T MRI-guided HIFU ablation studies in ex vivo porcine muscle/fat samples. The scanning parameters for the example high-intensity focused ultrasound (HIFU) ablation study in ex vivo tissues with an 8-element transducer were: Field of View (FOV) 109×109×48 mm³, matrix size 96×96×16, resolution 1.13×1.13×3 mm³, slice orientation axial, RF coils and channels (in addition to spine 12) were flexible 4, flip angles 3° and 34°, targeted $T_1$ range 300~1200 ms, number of echoes/$TE_1$/$\Delta TE$ 6/1.59/1.29 ms, TR 11.43 ms, number of segments 96, total running time 14.3 minutes, number of radial spokes in center/in total of KWIC filter 8/89, temporal resolution/temporal footprint of dynamic images 2.0/32.6 s. The scanning parameters for the example high-intensity focused ultrasound (HIFU) ablation study in ex vivo tissues with an 128-element transducer were: Field of View (FOV) 258×258×48 mm³, matrix size 224×224×16, resolution 1.15×1.15×3 mm³, slice orientation coronal, RF coils and channels (in addition to spine 12) were flexible 4, flip angles 5° and 29°, targeted $T_1$ range 300~1000 ms, number of echoes/$TE_1$/$\Delta TE$ 6/1.54/1.34 ms, TR 12.23 ms, number of segments 64, total running time 15.1 minutes, number of radial spokes in center/in total of KWIC filter 8/89, temporal resolution/temporal footprint of dynamic images 3.1/34.8 s.

In this example, HIFU experiments were conducted using a system with two transducers. The 128-element phased array transducer had a diameter of 90 mm, frequency of 1 MHz, a focal point of ~1×1×7 mm³, and a peak electrical power output of 1200 W. The 8-element annual array transducer had a diameter of 25 mm, frequency of 2.5 MHz, a focal point of ~0.7×0.7×3 mm³, and a peak electrical power output of 200 W. Two to four optical thermal probes were used to measure absolute temperature, with one to two being inserted into muscle and fat tissues respectively. 3D Cartesian gradient-echo $T_1$-weighted images (FOV=192× 192×64 mm³, matrix size=192×192×64, TE/TR=2.1/4.8 ms) were acquired before HIFU ablation to visualize the locations of the probes. $B_1+$ maps were acquired to calibrate flip angles prior to HIFU ablation. The HIFU focal point was positioned at the interface between muscle and fat. Temperature probe recording started 15 s before MRI acquisition, which started a further 1.75 minutes prior to HIFU ablation to establish a baseline. Each HIFU ablation lasted 8 minutes with an electrical power of 90 W using the 128-element transducer and 12 W using the 8-element transducer. After HIFU ablation concluded, MRI and temperature probe measurements continued for 4-6 minutes to observe the cooling down period. During reconstruction, the KWIC filter parameters were chosen to accommodate the smaller matrix size. It is noted the temporal resolution was lower when coronal slices were prescribed, as the scanner imposed a stricter specific absorption rate (SAR) limit, increasing TR compared to axial scans with the same TEs.

Figures 16A, 16B:
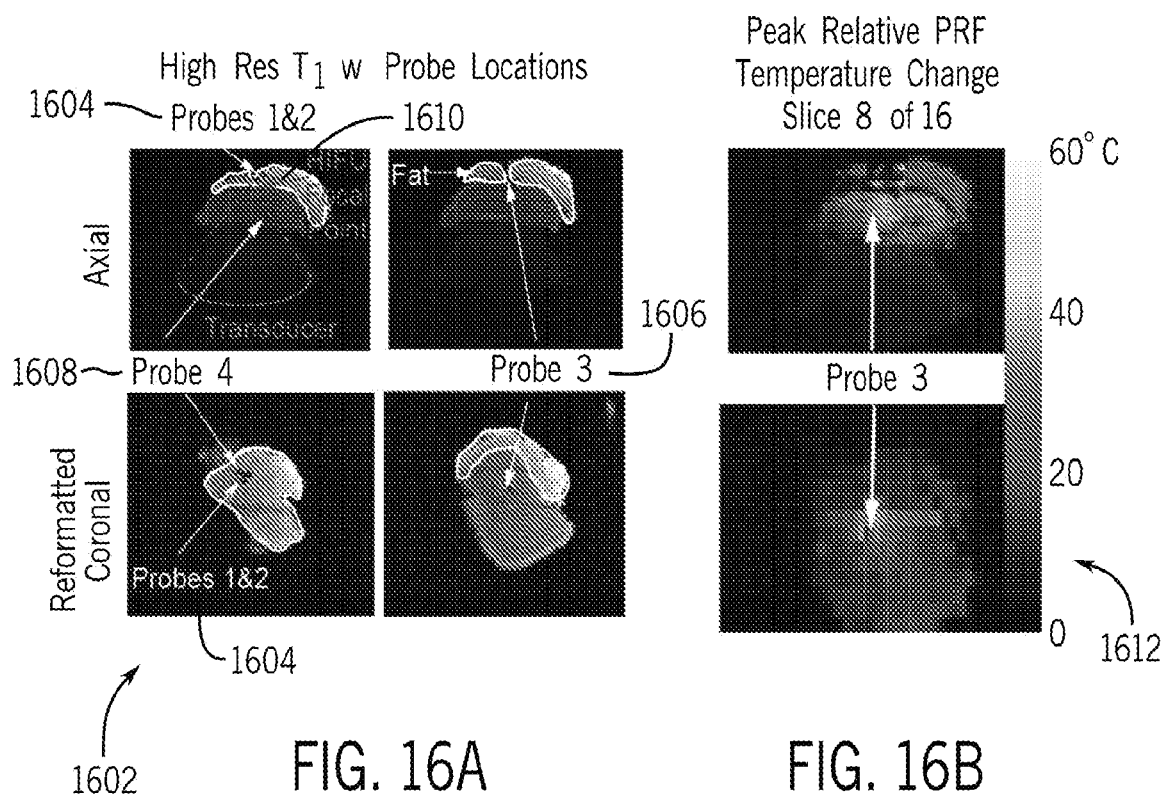
FIG. 16A shows example high-resolution $T_1$-weighted images of an ex vivo tissue sample showing the locations of two temperature probes in accordance with an embodiment.
FIG. 16B shows example axial and reformatted coronal maps of relative temperature changes as calculated by proton resonance frequency shift (PRF) across the sample at peak temperature right before the conclusion of HIFU ablation in accordance with an embodiment.
Figure 16C:
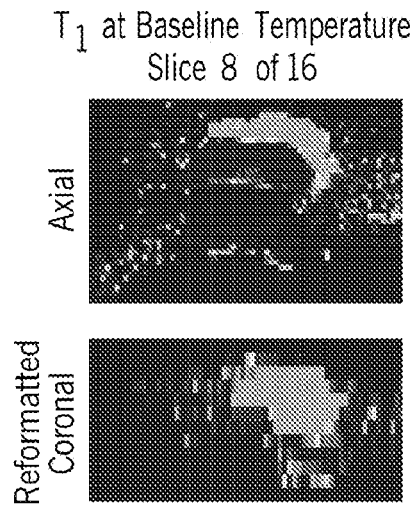
FIGS. 16C and 16D show example axial and reformatted coronal $T_1$ maps at baseline temperature and peak temperature in accordance with an embodiment.
Figure 16D:
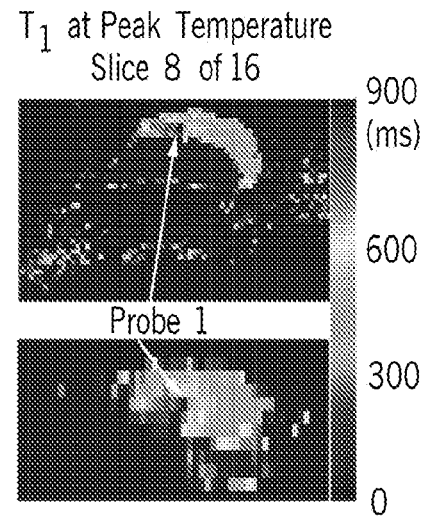
Figure 16E:
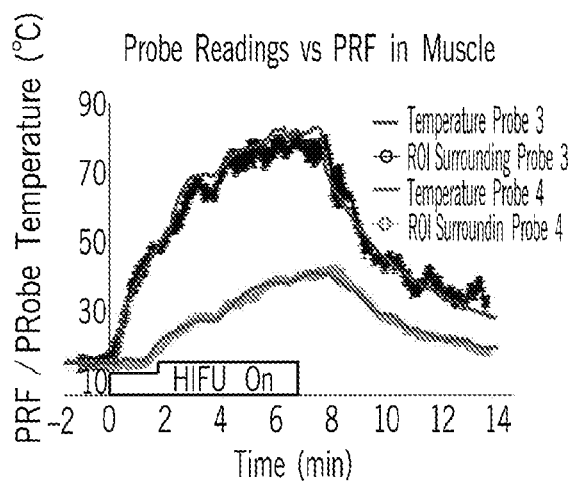
FIGS. 16E and 16F show example readings of temperature probes compared to adjacent PRF (muscle) and $T_1$ (fat) measurements in accordance with an embodiment.
Figure 16F:
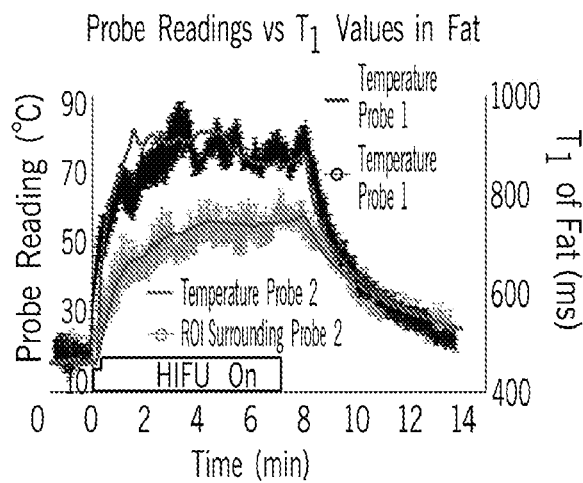

The results of the example high-intensity focused ultrasound (HIFU) ablation using the proposed radial VFA sequence with the 8-element transducer are shown in FIGS. 16A-16F. High-resolution $T_1$-weighted images 1602 (shown in FIG. 16A) of the tissue sample highlight the fat/muscle compartments. The signal voids 1604, 1606, 1608 caused by the temperature probes and the location of the focal point 1610 are shown in FIG. 16A. The temporal resolution was 2.9 s. The PRF temperature change map 1612 in the muscle at peak temperature during HIFU ablation is overlaid on the anatomical images in FIG. 16B. FIGS. 16C and 16D show the $T_1$ maps 1614, 1616 of the fat tissue at baseline and peak temperatures, respectively. The mean PRF temperature change and $T_1$ values 1618 in eight voxels surrounding the probes in FIG. 16E were compared to the temperature probe readings 1620 in FIG. 16F. The mean absolute difference between PRF temperature measurements and the temperature probe readings in muscle was 1.89° C. and 1.23° C. for probes 3 and 4, respectively. The temperature coefficient of $T_1$ for porcine fat around the locations of two temperature probes was calculated using least-squares linear regression method to be 7.78±0.19 ms/° C. (i.e., data in FIG. 16F), which is consistent with a previously reported value of 8 ms/° C. from literature.

As mentioned, an example high-intensity focused ultrasound (HIFU) ablation using an 128-element transducer in an ex vivo mixed porcine muscle/fat sample was also performed. In this example study, the SNR was lower than the study (discussed above) using the 8-element transducer because of the increased separation between sample and RF coils. A temporal resolution of 3.1 s was specified to accommodate the FOV and matrix size. The mean absolute difference between PRF temperature measurements and the temperature probe readings in muscle was 0.9° C. The temperature coefficient of $T_1$ for porcine fat in this sample was 8.11±0.25 ms/° C., consistent with the HIFU study using the 8-element transducer and literature values.

The proposed VFA multi-echo GA stack-of-radial MRI technique simultaneously measures PRF and $T_1$ for temperature mapping in aqueous and adipose tissues. The VFA 3D stack-of-radial acquisition has an intrinsic tolerance of undersampling which, coupled with the usage of KWIC reconstruction, reduced the number of radial spokes needed in the center of k-space and enhanced temporal resolution. In the example non-heating in vivo scans described above, the sequence achieved full 3D coverage of brain, prostate and breasts (FOV of up to 350×350×240 mm³), isotropic in-plane resolution of 1.1×1.1 to 1.3×1.3 mm², and temporal resolution of 2-5 s per 3D volume without the need for breath-holding. In an embodiment, bipolar multiple-echo acquisitions allowed for quantification of fat/water maps, which helped to decide where to utilize PRF or $T_1$ measurements for temperature mapping. In an embodiment, magnitude and phase images of all echoes were combined to boost SNR and reduce temperature mapping errors. Standard deviation (SD) of PRF temperature changes in aqueous tissues remained below 3° C. after the correction of $B_0$ field drift, despite the larger flip angle not being the optimal Ernst angle. $T_1$ maps were stable over time in tissue types for which we optimized the variable flip angles, as evidenced by $T_1$ COV<5% during the 20-30-minute experiments.

When applied to monitor ex vivo HIFU ablation (in the example described above), the proposed radial VFA sequence was able to image a 3D volume encompassing the sample every 3 s depending on the size of the sample. PRF temperature change in muscle closely tracked thermal probe readings, with its deviation matching the precision of 1-2° C. using clinical PRF temperature mapping methods with comparable temporal and spatial resolutions for monitoring ablation. On the other hand, the temperature coefficient of $T_1$ of fatty tissues agreed well with previously reported value of 8 ms/° C. If this value was used to convert $T_1$ change into temperature change, it would yield a mean absolute difference of 1.99° C. and 1.82° C. from the readings of temperature probes of 3 and 4, respectively, and a mean absolute difference of 2.22° C. from the readings of temperature probe 2. In an embodiment, the flip angles may be optimized for muscle and aqueous tissues so that $T_1$ may be used to calculate temperature change with PRF in a mutually constrained manner to improve accuracy. This, however, is likely to decrease the accuracy of measured $T_1$ in both tissue compartments, which can be addressed by the addition of another intermediate flip angle at the expense of temporal resolution. The radial VFA sequence may also be readily modified to only use the larger flip angle to produce dynamic $T_1$-weighted images in settings where qualitative results suffice, such as to observe the irreversible tissue coagulation during ablation.

Example 2

In another example study, non-heating free-breathing scans were carried out in human subjects to evaluate the reliability of both $T_1$ and PRF measurements in a moving organ, in particular, the liver. In this study, N=10 healthy subjects (6 males, 4 females) with age of 33±11 years and body mass index of 28.4±8.8 kg/m$^2$ underwent non-heating free-breathing abdominal scans at 3T with body and spine arrays for 5~10 minutes. The scanning parameters for the example in vivo dynamic PRF/$T_1$ thermometry were: Field of View (FOV) 320×320×48 mm$^3$, matrix size 192×192×16, resolution 1.67×1.67×3 mm$^3$, flip angles 3° and 15°, targeted $T_1$ range 800~1200 ms, number of echoes/$TE_1$/$\Delta TE$ 4/1.21/1.21 ms, TR 6.32 ms, number of angles/segment 32, number of segments 48, total running time 6:36 (minutes:seconds), number of radial spokes in center/total spokes 8/144, temporal resolution/temporal footprint of PRF maps 0.91/16.4 s, temporal resolution/temporal footprint of $T_1$ maps 0.91/20.5 s.

To characterize the stability of radial VFA thermometry, the temporal coefficient of variation (COV) of $T_1$ was calculated on slices that were observed at all time points as the ratio between the standard deviation and the mean of $T_1$ during the entire scan, and the temporal standard deviation (SD) of PRF temperature change was calculated on the same slices. One region of interest (ROI) of 2 cm$^2$ was drawn in each subject in one of these slices to track $T_1$ and PRF fluctuations. Different choices of temporal resolution and footprint of the KWIC filter were first chosen to study their impact on the ability to resolve liver motion and PRF/$T_1$ measurement accuracy and to decide on a combination that achieved acceptable performance. For comparison, dynamic $T_1$ maps were also calculated by using only end-expiration $B_1+$ maps using only a single baseline phase image acquired at end-expiration, while dynamic PRF temperature changes were calculated by using only a single set of baseline phase images during the coil- and echo-combination step of KWIC reconstruction to evaluate the advantages of the proposed methods.

Figure 17:
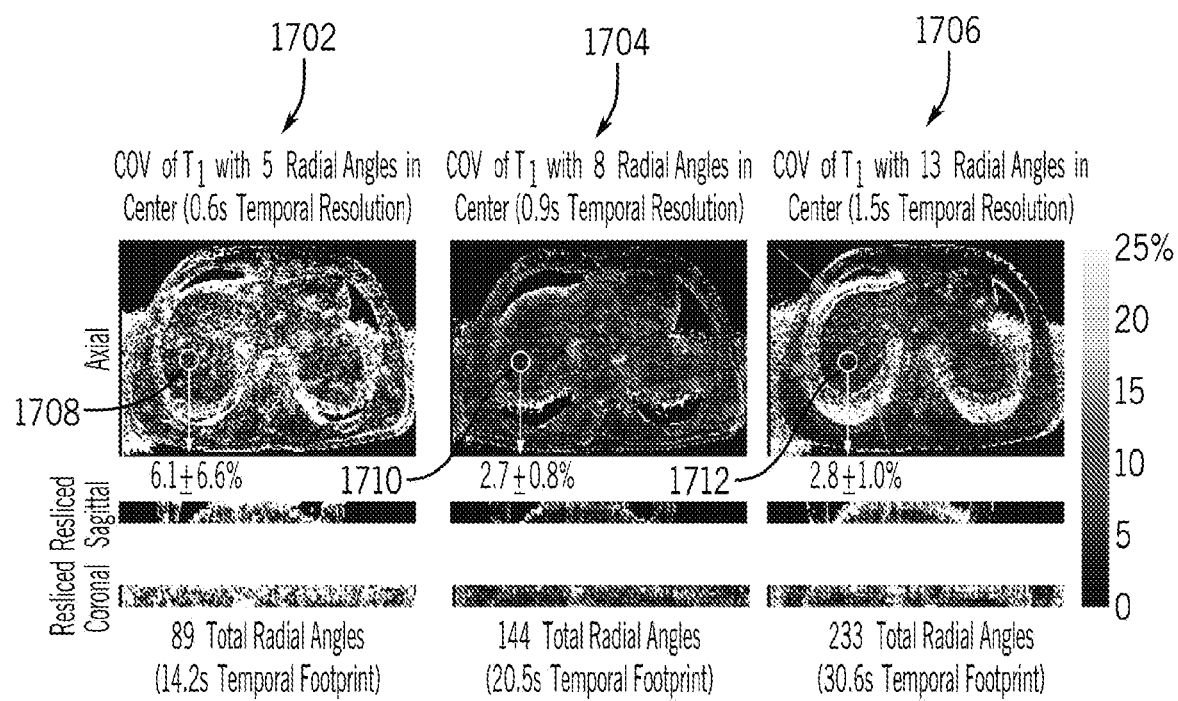
FIG. 17 shows example temporal coefficient of variation (COV) maps from a non-heating free-breathing liver scan using different k-space weighted image contrast (KWIC) filter settings in accordance with embodiment.

FIG. 17 shows example prescribed axial and resliced sagittal and coronal COV maps 1702, 1704, 1706 of $T_1$ measurements in one of the human subjects using different combinations of temporal resolution and footprint. Flip angle imperfection was compensated for by using dynamic interpolated $B_1+$ maps. The circles 1708, 1710, 1712 highlight the regions of interest (ROIs) in which the mean±SD of the COV of $T_1$ during the entire scan was calculated. Map 1702 included the fewest number of radial angles in the KWIC filter, which was able to capture the movement of the liver well with the highest temporal resolution but suffered from streaking artifacts and led to high COV value in the $T_1$ maps. Map 1706, on the contrary, included the most radial angles in the KWIC filter to generate the best image quality and low COV value. However, the prolonged temporal resolution and footprint was not able to capture the movement of the liver and led to motion blurring and errors in the $T_1$ maps, especially around the edges of the liver as pointed to by the blue arrows. A desirable balance was successfully reached in map 1704 with a temporal resolution of 0.9 s and temporal footprint of 20.5 s that yielded low COV for $T_1$ while avoiding the temporal blurring effect. This KWIC filter setting was used throughout the rest of the analysis.

Figure 18:
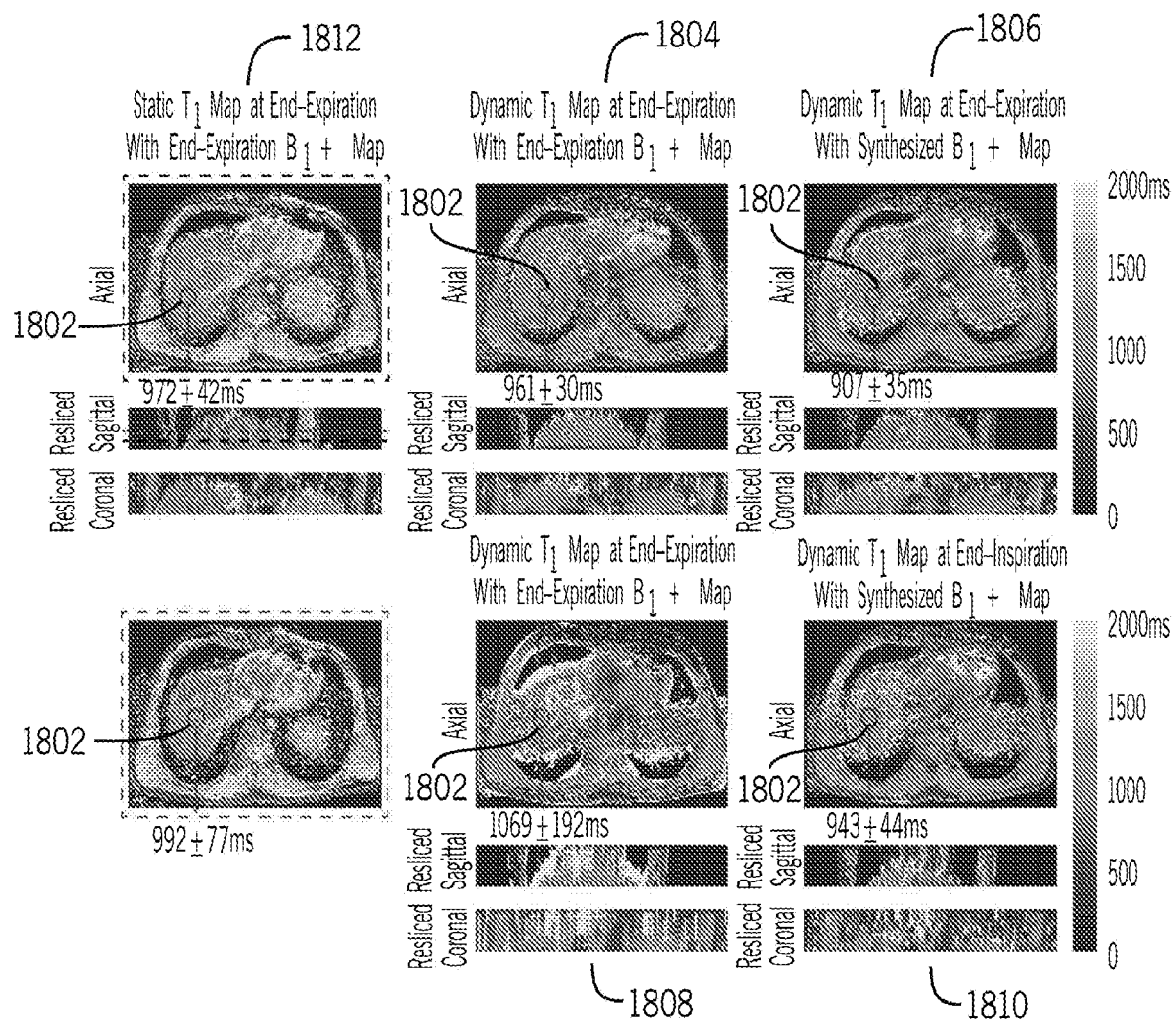
FIG. 18 shows example $T_1$ maps acquired from a subject using an optimized KWIC filter setting in accordance with an embodiment.

FIG. 18 shows example $T_1$ maps acquired from a subject using an optimized KWIC filter setting in accordance with an embodiment. For comparison, static $T_1$ maps 1812 were calculated using a non-segmented radial VFA sequence with a soft-gating technique to reconstruct images with the liver at end-expiration position in the same subject. Circles 1802 shows the mean±SD of $T_1$ reading in a region of interest (ROI) which was used as a reference. Dynamic $T_1$ maps 1804, 1806, 1808, 1810 were reconstructed using the same KWIC setting as map 1704 (shown in FIG. 17). At dynamic time points when the liver was at the end-expiration position, using the static end-expiration 1812 and the interpolated $B_1+$ maps yielded similar $T_1$ measurements, both comparable with the static $T_1$ map 1812. However, at dynamic points when the liver was at the end-inspiration position, the use of static end-expiration $B_1+$ maps created a mismatch with magnitude images and led to errors in $T_1$ measurement. The interpolated dynamic $B_1+$ map, on the other hand, yielded more accurate $T_1$ values in compared to the static $T_1$ map 1812.

Figure 19:
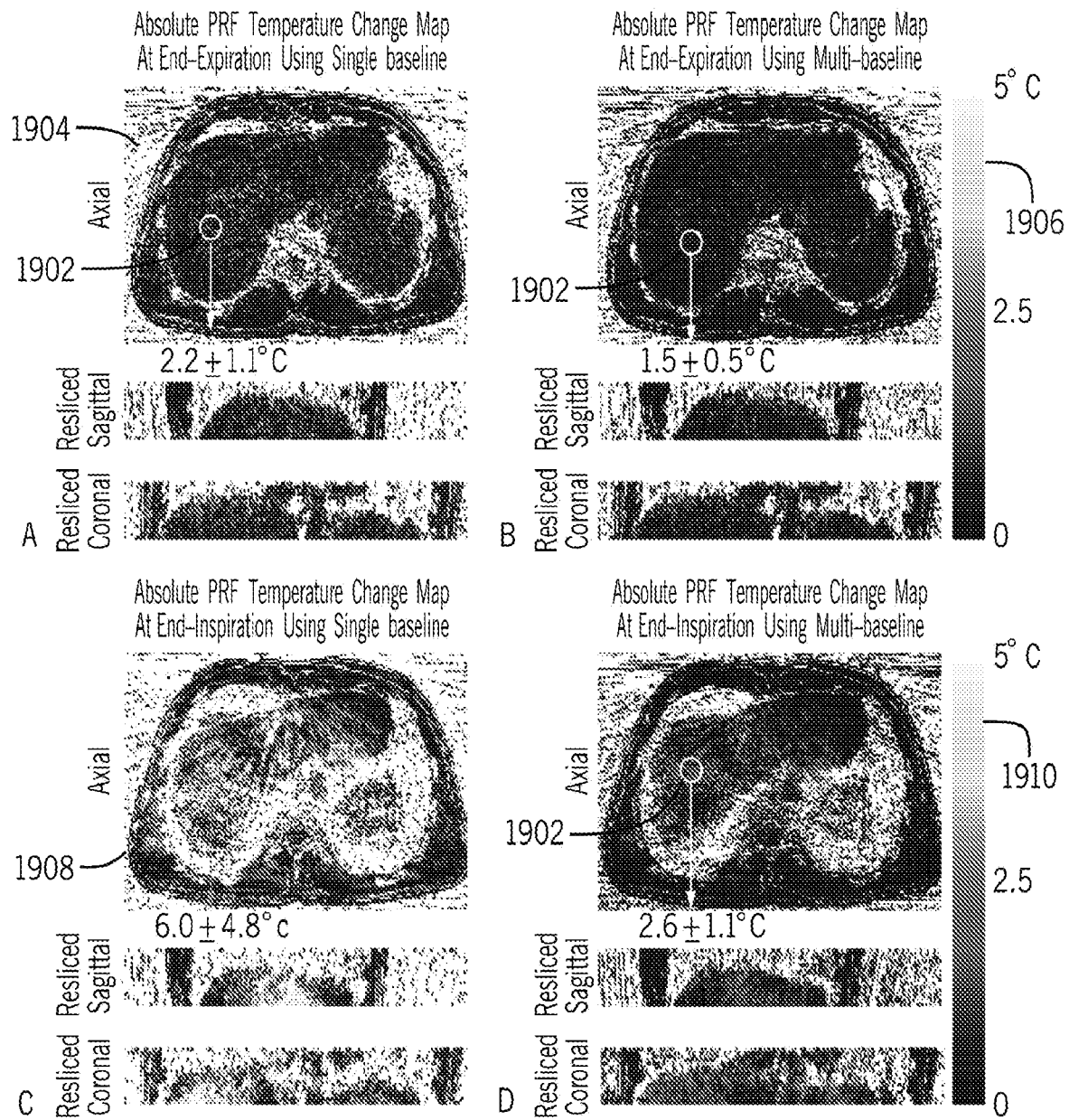
FIG. 19 shows example absolute relative PRF temperature change maps with the liver at different breathing stages in accordance with an embodiment.

The absolute PRF temperature change maps in the same subject using different coil-combination methods are shown in FIG. 19 and were determined by using single baseline with the liver in the end-expiration position and multi-baseline library during the echo- and coil-combination step during KWIC phase image reconstruction. FIG. 19 shows example absolute relative PRF temperature change maps 1904, 1906, 1908, 1910 with the liver at different breathing stages in accordance with an embodiment. Circles 1902 show an ROI in which the mean±SD of absolute PRF temperature change was calculated. At dynamic time points when the liver was also at the end-expiration position, both methods showed similarly small apparent PRF temperature change. The single-baseline method yielded slightly higher temperature error, possibly due to slight mismatch in liver position between baseline and dynamic time points, which could be reduced by using a library of baseline images. However, at dynamic time points when the liver was at the end-inspiration position, single-baseline method gave much higher temperature error, while a multi-baseline method still achieved good stability of PRF temperature measurements, even near the dome of the liver where motion and magnetic susceptibility gradients were more impactful.

In the non-heating free-breathing liver scans of this example, the radial VFA technique achieved 3D coverage (16 slices), in-plane resolution of 1.6×1.6 mm², and temporal resolution of <1 s. The use of dynamic synthesized $B_1+$ maps for VFA $T_1$ calculation and multi-baseline PRF approach substantially improved the stability of both PRF and $T_1$ measurements compared to reference approaches. COV of $T_1$ and SD of PRF temperature change were below 5% and 2.5° C., respectively, throughout the 6-minute scans even in the liver dome, which experienced prominent motion. Some blurring could be observed near liver boundaries due to the 15~20 s temporal footprint of the KWIC filter. This could be reduced by incorporating parallel imaging acceleration.

Example 3

In another example study, the VFA 3D stack-of-radial multi-echo gradient echo MRI technique ("radial VFA") was used for simultaneous free-breathing 3D liver $T_1$, PDFF, and $R_2^*$ mapping. In this example, healthy adults (n=18) and children (n=2) were imaged at 3 Tesla using radial VFA in 3-min. $B_1+$ maps were acquired during end-expiration breath-holds for VFA $T_1$ calculation. PDFF/$R_2^*$ were calculated from multi-echo data acquired with the smaller flip angle. Self-navigated soft-gating was performed to reconstruct radial VFA images at end-expiration. Breath-holding VFA 3D Cartesian multi-echo gradient echo and breath-holding 2D Cartesian Modified Look-Locker Inversion Recovery (MOLLI) sequences were acquired as references. Bland-Altman analysis was conducted to evaluate agreement between the sequences. Intraclass correlation coefficients (ICC) were calculated to assess the repeatability of radial VFA.

To assess the $T_1$ mapping accuracy, a system $T_1/T_2$ phantom was placed in a 3T scanner at 25° C. for an hour and scanned using the proposed radial VFA method twice with 20 minutes in between. Reference scans were acquired with 3D Cartesian VFA and 2D Cartesian MOLLI sequences. The scanning parameters were matched with those used in in vivo experiments, except that the number of slices was set to 64 to cover the entire phantom. The scanning parameters for the free-breathing radial VFA scan were: FOV 320×320×96 mm³, matrix size 256×256×32, flip angles 3 and 18, target $T_1$ 1000 ms, number of echoes/$TE_1$/$\Delta TE$ (ms) 6/1.41/1.29, TR (ms) 9.84, total number of radial angles 256 per flip angle, radial undersampling factor 1.57, total acquisition time 3 min 4 s. A simulated sinusoidal self-gating signal with a frequency of 0.2 Hz was processed and applied to the raw k-space data during image reconstruction to ensure a similar level of undersampling as in vivo experiments. Regions of interest (ROIs) of 25 voxels in size were drawn in the four samples whose $T_1$ ranged from 700 ms to 1500 ms (consistent with liver $T_1$). The flip angles for the radial VFA and Cartesian VFA sequences were designed for this range of $T_1$. The mean and standard deviation (SD) of measured $T_1$ in these samples were calculated to compare results acquired from all protocols.

In this example study, the subjects were 18 healthy adults (11 males and 7 females) aged 33.3±3.4 years with body mass index (BMI) of 24.2±3.1 kg/m², and 2 healthy children (2 males) aged 17±0 years with BMI of 24.7±0.4 kg/m². All subjects underwent scans at 3 Tesla with an anterior 18-channel flexible array coil in combination with 12 to 16 elements of the spine array coil. Two free-breathing (FB) radial VFA scans were acquired more than 10 minutes apart to assess its intra-session repeatability. With a TR of 9.4 ms, a total of 32 slices plus 8.3% oversampling resulted in a temporal resolution of 330 ms for the motion self-navigation signals, which was sufficient for tracking breathing motion. The radial VFA technique was designed to match the Cartesian VFA protocol and provide coverage for a large portion of the liver, which included the entire liver dome. To calibrate flip angles for VFA $T_1$ fitting, $B_1+$ maps were acquired during breath-holding at end-expiration. As references, two 3D Cartesian multi-echo gradient-echo scans with the same variable flip angles as radial VFA were acquired during two separate breath-holds (BH) at end-expiration, and one 2D Cartesian MOLLI scan was acquired during another BH at end-expiration. BH Cartesian VFA $T_1$ maps were calculated in a similar manner as FB radial VFA. BH Cartesian PDFF and $R_2^*$ maps were reconstructed on the scanner from the BH Cartesian VFA dataset with the smaller flip angle with a multi-step nonlinear fitting procedure with a multi-peak fat spectral model. Field of view (FOV) and matrix size were adjusted to accommodate the body sizes of each subject. The number of radial angles was set to be the same as the image matrix size, resulting in 1.57-fold undersampling based on Nyquist sampling criteria.

In each subject, circular ROIs with area of 5 cm² were drawn in 3 slices (liver dome, mid-section, and lower-section) near corresponding landmarks in FB radial VFA and BH Cartesian VFA acquisitions. Bland-Altman analysis was used to evaluate the agreement in $T_1$, PDFF, and $R_2^*$ by determining the mean difference (MD) and 95% limits of agreement (LoA=MD±1.96×SD) between self-gating motion-compensated FB radial VFA and BH Cartesian VFA. 12 additional ROIs were drawn on slices imaged by both self-gating motion-compensated FB radial VFA and BH Cartesian MOLLI acquisitions to evaluate $T_1$ agreement using Bland-Altman analysis. The intraclass correlation coefficients (ICC) between the repeated self-gating motion-compensated FB radial VFA $T_1$, PDFF, and $R_2^*$ mapping results was calculated using the same ROIs.

Figure 20:
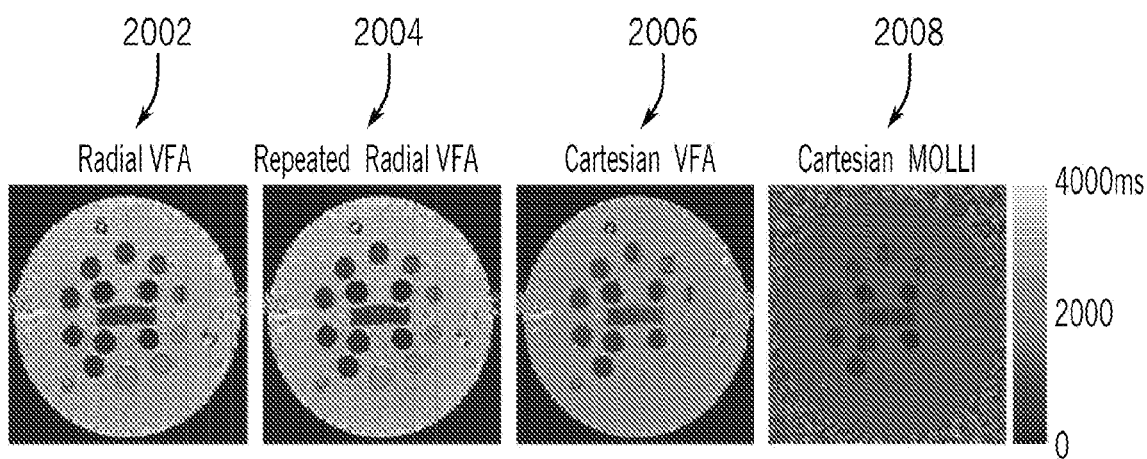
FIG. 20 shows example $T_1$ maps acquired from the system $T_1/T_2$ phantom using multiple sequences in accordance with an embodiment.
Figure 21:
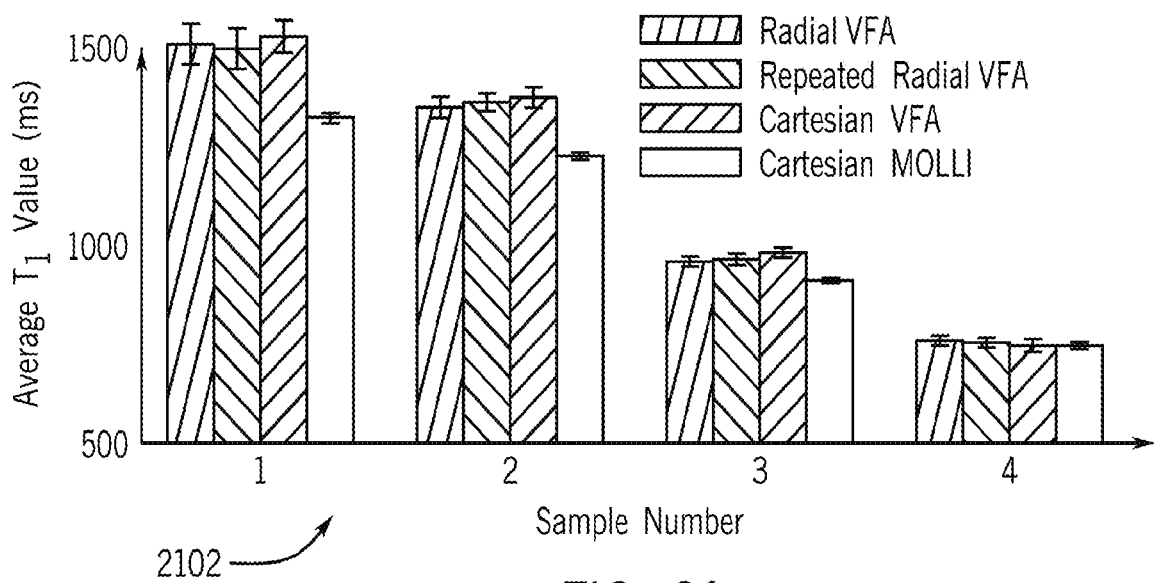
FIG. 21 is a bar graph comparing $T_1$ values acquired with each of the sequences of FIG. 15 in a phantom in accordance with an embodiment.

FIG. 20 shows example $T_1$ maps acquired from the system $T_1/T_2$ phantom using radial VFA 2002, repeated radial VFA 2004, Cartesian VFA 2006 and Cartesian MOLLI 2008. $T_1$ ranged from 600 ms to 1500 ms. FIG. 21 shows a bar graph 2100 of mean and standard deviation SD of $T_1$ measured in each of the sequences. The radial VFA method demonstrated good repeatability, and radial VFA and Cartesian VFA methods exhibited good agreement. Cartesian MOLLI had lower $T_1$ measurements than both VFA protocols in all four samples as well as in the background water bath.

Figure 22:
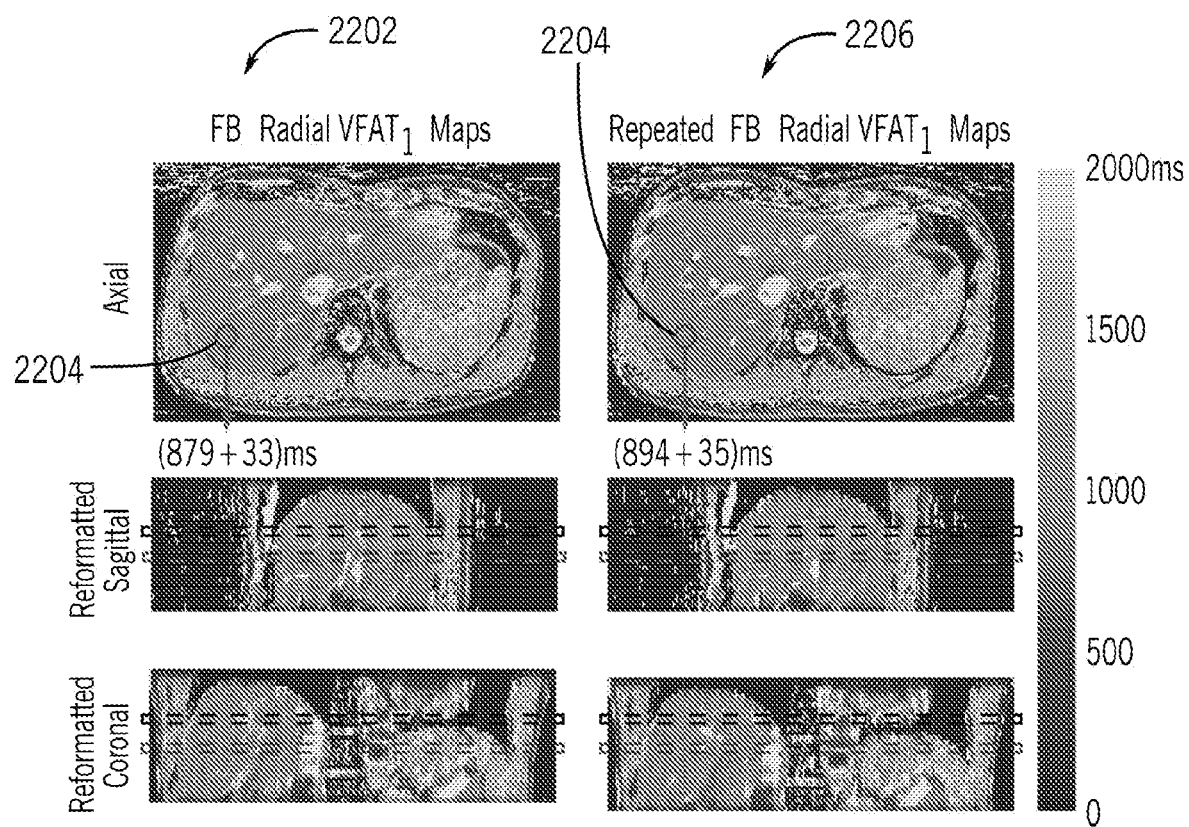
FIG. 22 shows example axial, reformatted sagittal and reformatted coronal liver $T_1$ maps acquired using a free-breathing variable flip angle 3D stack-of-radial technique in accordance with an embodiment.
Figure 23:
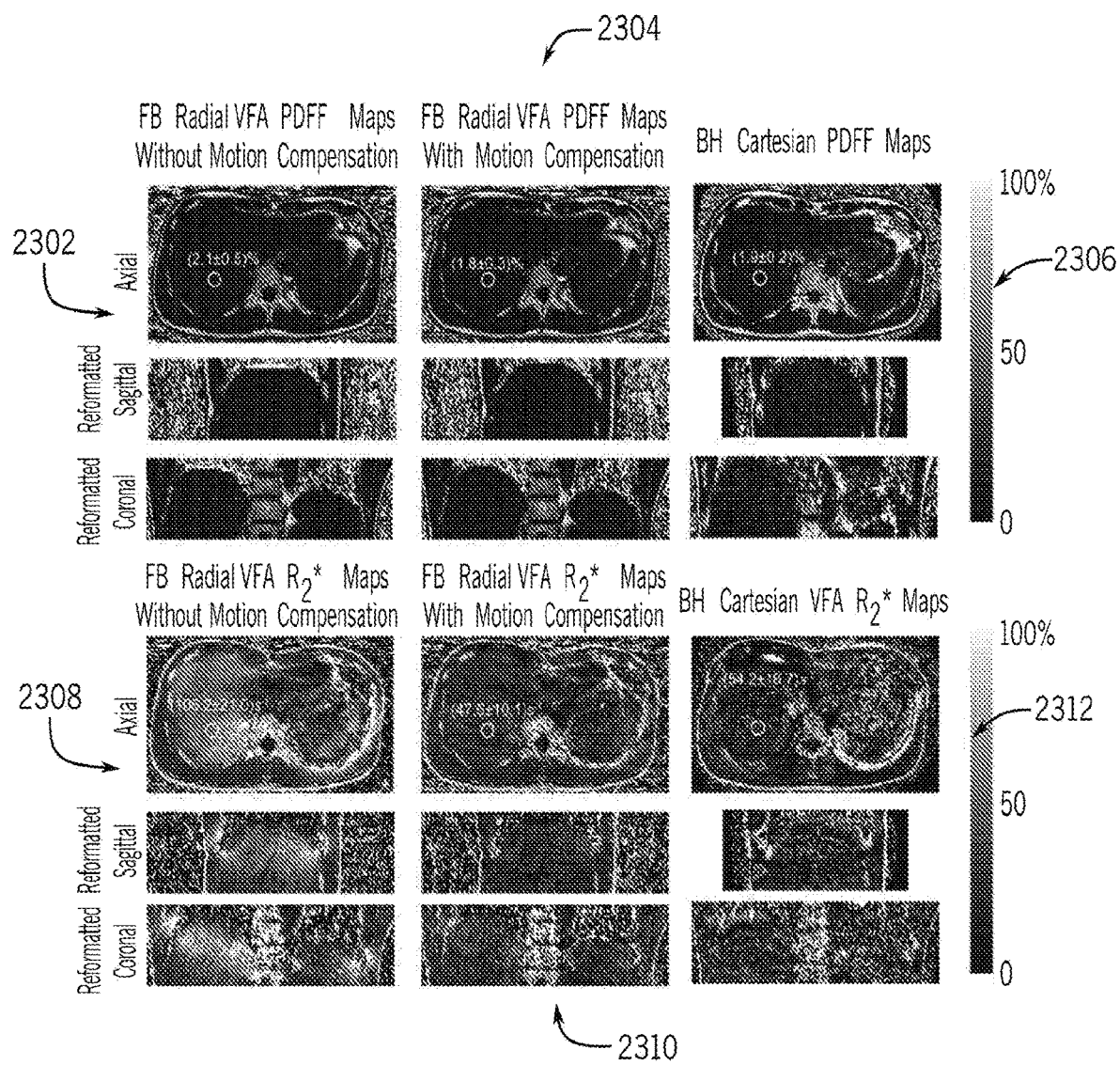
FIG. 23 shows example liver proton density fat fraction (PDFF) and $R_2^*$ maps acquired using a free-breathing variable flip angle 3D stack-of-radial technique in accordance with an embodiment.

$T_1$ mapping results 2202, 2206 in one healthy male adult subject in the prescribed axial as well as reformatted sagittal and coronal orientations using the FB radial VFA are shown in FIG. 22. The mean $T_1$ measured from the ROI 2204 was consistent between different methods. The repeated FB radial VFA 2204 scans with self-gating motion compensation showed sharp delineation of the liver dome and the air space around it. FIG. 23 shows the PDFF and $R_2^*$ mapping results in the same healthy adult subject as in FIG. 22. For PDFF, both motion-averaged 2302 and self-gating motion-compensated 2304 FB radial VFA results have similar mean PDFF values compared to BH Cartesian 2306. BH Cartesian PDFF maps 2306 showed a higher level of noise, especially in the reformatted sagittal and coronal views. Motion averaging for FB radial VFA led to artificially elevated and non-uniform $R_2^*$ values 2308 in the liver, while FB radial VRF with self-gating motion compensation yielded $R_2^*$ values 2310 that agreed with those obtained by the BH Cartesian protocol 2312. As is observed in PDFF maps, BH Cartesian $R_2^*$ maps also displayed a higher noise level.

In this example study, $T_1$ mapping results in a healthy pediatric subject showed good repeatability of the FB radial VFA technique in the example ROI as well as agreement with other BH Cartesian protocols. Compared with adult subjects, pediatric subjects had more difficulty holding their breath for 20 s. As a result, BH Cartesian VFA exhibited errors in $T_1$ measurements near the dome of the liver. PDFF and $R_2^*$ mapping results were acquired for the same healthy pediatric subject. FB radial VFA PDFF maps with self-gating was consistent with BH Cartesian results. However, the BH Cartesian PDFF maps were noisier and had more visible motion artifacts than self-gating motion compensated FB radial VFA PDFF maps. Improvements in the FB radial VFA $R_2^*$ mapping results with self-gating were appreciated in comparison to motion-averaged FB radial VFA $R_2^*$ maps, since the bright artifacts near the liver dome that were also seen in adult subjects are greatly suppressed. Self-gating motion compensated FB radial VFA and BH Cartesian $R_2^*$ maps were also in agreement.

In this study, a golden-angle-ordered 3D stack-of-radial multi-echo gradient-echo sequence with variable flip angle acquisition was used for free-breathing simultaneous $T_1$, PDFF, and $R_2^*$ mapping in the liver. Evaluations in phantom and healthy human subjects have shown quantitative agreement with $T_1$, PDFF, and $R_2^*$ measured by reference breath-holding Cartesian VFA and MOLLI protocols. The radial VFA technique also demonstrated good intra-session repeatability despite the effects of potential bulk and respiratory motion.

The soft-gating employed with the radial VFA technique may lead to a better utilization of the acquired k-space data and a lesser degree of undersampling. Thresholding the soft-gated motion signal may also minimize the impact of outliers (such as inadvertent deep breaths) while avoiding artifacts caused by discontinuities in golden-angle ordering in the case of high rejection rates. The application of motion compensation corrected for the artificially elevated $R_2^*$ values observed in the motion-averaged FB radial VFA $R_2^*$ maps. The soft-gated FB radial VFA $R_2^*$ mapping results were also in good agreement with the BH Cartesian results across all subjects. Moreover, FB radial VFA with self-gating motion compensation was able to generate $R_2^*$ maps with minimal noise and artifacts. In contrast, the $R_2^*$ maps of BH Cartesian VFA were considerably noisier and/or had visible artifacts, which may be caused by the subject not being able to hold his/her breath for the entire duration of the scan (20 s) and the parallel imaging acceleration factors (factor of 3 along phase encoding direction). PDFF mapping was more robust to motion. As a result, motion compensation may not be needed for FB radial VFA if the primary goal is to measure PDFF.

The stack-of-radial acquisition adopted in the radial VFA technique has the advantage of enabling free-breathing scans, which may be of use in patients who are unable to suspend respirations such as the elderly, the sick and the very young. As a result, more accurate data may be obtained with FB radial VFA to assist with diagnosis and prognosis of liver diseases. In addition, the FB radial VFA technique produces measurements that can be compared between scans acquired at different times and thus may facilitate longitudinal monitoring and management of liver diseases with the three quantitative MRI parameters. In an embodiment, parallel imaging techniques and other acceleration strategies can be incorporated to further reduce scanning time. Higher acceleration factors can also be used to increase the spatial coverage without compromising the temporal resolution of the self-navigation signal. In an embodiment, the radial VFA technique may perform multiparametric MRI quantification of liver disease without the need for breath-hold imaging or biopsy.

Computer-executable instructions for free-breathing quantitative multiparametric MRI using a variable-flip-angle multi-echo gradient-echo golden-angle-ordered 3D stack-of-radial sequence according to the above-described methods and examples may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for proton resonance frequency shift (PRF) and $T_1$-based temperature mapping using a magnetic resonance imaging (MRI) system, the method comprising:
    acquiring, using the MRI system, a set of magnetic resonance (MR) data from a region of interest of a subject by performing a variable-flip-angle multi-echo gradient-echo 3D stack-of-radial pulse sequence, wherein the variable-flip-angle multi-echo gradient-echo 3D stack-of-radial pulse sequence is configured to acquire radial k-space data in a plurality of segments, each segment alternatively acquired with each of a plurality of flip angles;
    generating at least one $T_1$ map based on the set of MR data;
    generating at least one PRF temperature map based on the set of MR data;
    generating at least one $T_1$-based temperature map based on the set of MR data; and
    displaying the PRF temperature map and the $T_1$-based temperature map.

2. The method according to claim 1, further comprising applying a sliding-window k-space weighted image contrast (KWIC) filter to the set of MR data associated with each flip angle of the plurality of flip angles for image reconstruction.

3. The method according to claim 1, wherein acquiring the set of MR data further comprises using radial sampling in a $k_x$-$k_y$ plane and Cartesian encoding along $k_z$.

4. The method according to claim 1, wherein the at least one PRF temperature map is for an aqueous tissue.

5. The method according to claim 1, wherein the at least one $T_1$-based temperature map is for an adipose tissue.

6. The method according to claim 1, wherein the at least one PRF temperature map and the at least one $T_1$-based temperature map are generated simultaneously.

7. The method according to claim 1, wherein generating at least one $T_1$-based temperature map comprises:
   generating a set of complex images of all echoes and using a fat and water separation for the plurality of flip angles to generate a fat mask; and
   calculating at least one $T_1$ map using a magnitude component in an adipose tissue identified in the fat mask.

8. The method according to claim 1, further comprising applying a parallel imaging technique for image reconstruction.

9. The method according to claim 1, further comprising applying a reconstruction technique with low-rank or sparsity constraints for image reconstruction.

10. The method according to claim 1, wherein the variable-flip-angle multi-echo gradient-echo 3D stack-of-radial pulse sequence uses golden-angle ordering.

11. The method according to claim 1, further comprising applying self-navigation and motion compensation for image reconstruction.

12. A magnetic resonance imaging system comprising:
   a magnet system configured to generate a polarizing magnetic field about at least a portion of a subject;
   a magnetic gradient system including a plurality of magnetic gradient coils configured to apply at least one magnetic gradient field to the polarizing magnetic field;
   a radio frequency (RF) system configured to apply an RF field to the subject and to receive magnetic resonance signals from the subject using a coil array; and
   a computer system programmed to:
      acquire a set of magnetic resonance (MR) data from a region of interest of a subject by performing a variable-flip-angle multi-echo gradient-echo 3D stack-of-radial pulse sequence, wherein the variable-flip-angle multi-echo gradient-echo 3D stack-of-radial pulse sequence is configured to acquire radial k-space data in a plurality of segments, each segment alternatively acquired with each of a plurality of flip angles;
      generate at least one $T_1$ map based on the set of MR data;
      generate at least one PRF temperature map based on the set of MR data;
      generate at least one $T_1$-based temperature map based on the set of MR data; and
      display the PRF temperature map and the $T_1$-based temperature map.

* * * * *